United States Patent
Kaneko et al.

(10) Patent No.: US 6,656,486 B2
(45) Date of Patent: Dec. 2, 2003

(54) COMPOSITIONS FORMING FILM SOLIDIFYING IN WATER AND NAIL-CARE PRODUCTS AND NAIL-CARE METHOD WITH THE USE OF THE SAME

(75) Inventors: Katsuyuki Kaneko, Kanagawa (JP); Ryota Yamasaki, Kanagawa (JP); Toshihito Yabu, Kanagawa (JP); Isamu Kaneda, Kanagawa (JP); Toshio Yanaki, Kanagawa (JP); Yoshikazu Soyama, Kanagawa (JP)

(73) Assignee: Shiseido Co., Ltd., Tokyo (JP)

( * ) Notice: Subject to any disclaimer, the term of this patent is extended or adjusted under 35 U.S.C. 154(b) by 0 days.

(21) Appl. No.: 09/959,309

(22) PCT Filed: Mar. 1, 2001

(86) PCT No.: PCT/JP01/01560

§ 371 (c)(1),
(2), (4) Date: Oct. 23, 2001

(87) PCT Pub. No.: WO01/64170

PCT Pub. Date: Sep. 7, 2001

(65) Prior Publication Data

US 2003/0095934 A1 May 22, 2003

(30) Foreign Application Priority Data

| Mar. 1, 2000 | (JP) | 2000-55846 |
| Oct. 31, 2000 | (JP) | 2000-333784 |
| Oct. 31, 2000 | (JP) | 2000-333785 |

(51) Int. Cl.$^7$ ............... A61K 6/00; A61K 7/00; A61K 7/04
(52) U.S. Cl. ............... 424/401; 424/61
(58) Field of Search ............... 424/61, 401

(56) References Cited

U.S. PATENT DOCUMENTS

| 4,126,675 A | * | 11/1978 | Boulogne et al. ............. 424/61 |
| 4,186,020 A | * | 1/1980 | Wachtel ............. 106/22 |
| 4,798,720 A | | 1/1989 | Holder |
| 5,939,468 A | * | 8/1999 | Siddiqui ............. 523/161 |
| 6,177,065 B1 | * | 1/2001 | Sekine et al. ............. 424/61 |

OTHER PUBLICATIONS

Japanese Patent Office, "Patent Abstracts of Japan," Publication No.: 09–071512, Date of Publication: Mar. 18, 1997, Application No.: 07–297428, Date of Filing: Oct. 20, 1995.

Japanese Patent Office, "Patent Abstracts of Japan," Publication No.: 08–225434, Date of Publication: Sep. 3, 1996, Application No.: 07–032101, Date of Filing: Feb. 21, 1995.

Japanese Patent Office, "Patent Abstracts of Japan," Publication No.: 03–044311, Date of Publication: Feb. 26, 1991, Application No.: 01–177176, Date of Filing: Jul. 11, 1989.

Japanese Patent Office, "Japanese Patent Application Gazette," Publication No.: 47–43348, Date of Publication: Dec. 19, 1972, Application No.: 46–31876, Date of Filing: May 12, 1971.

* cited by examiner

Primary Examiner—Thurman K. Page
Assistant Examiner—S. Howard
(74) Attorney, Agent, or Firm—Snider & Associates; Ronald R. Snider (57) ABSTRACT

The object of the present invention is to provide a film composition which is solidified in water of which a painted film is rapidly solidified and also has proper usabilities for use as a manicure. To accomplish the object a film composition of the present invention comprises water insoluble film materials, and a solvent which dissolves the water insoluble film materials and soluble with water, wherein the solvent contains specified alkylene glycol ethers and ketones, and characterized by that the film materials are precipitated from the mixture of the remaining solvent and penetrating water in a painted film of the composition when the painted film is dipped in water.

46 Claims, 2 Drawing Sheets

(A) Application (B) Dipping in water

(C) Dried

Fig. 1

(A) Application

(B) Dipping in water (C) Dried

Fig. 2

COMPOSITIONS FORMING FILM SOLIDIFYING IN WATER AND NAIL-CARE PRODUCTS AND NAIL-CARE METHOD WITH THE USE OF THE SAME

This application claims the priority of Japanese Patent Application No. 2000-55846 filed on Mar. 1, 2000, Japanese Patent Application No. 2000-333784 filed on Oct. 31, 2000 and Japanese Patent Application No. 2000-333785 filed on Oct. 31, 2000 which are incorporated herein by references.

TECHNICAL FIELD

The present invention relates to a film composition which is solidified in water, a manicure using the same and a manicuring method. In particular, the present invention relates to an improvement of a solvent of a composition of which the film is rapidly solidified in water.

BACKGROUND ART

Film compositions used as a nail enamel, a nail enamel base coat, a nail enamel over coat or the like are composed of water insoluble film materials, such as nitrocellulose, which is dissolved in organic solvents, such as ethyl acetate, butyl acetate or acetone.

A manicure is also a film composition. Some properties are needed for a manicure in relation to a film appearance and a film forming process. For example, a proper color tone and a proper gloss of a film are needed. Further, properties such as
(1) a proper viscosity for applying a nail with ease
(2) a rapid drying speed of a film after it is applied on a nail and a formation of an uniform film surface on the nail, and
(3) a sufficient adhesion to the nail
are also needed. In these properties a rapid drying speed after applying on a nail and a formation of an uniform film surface are closely related to each other. Namely, if a drying speed of a manicure after applying on a nail is too rapid, a viscosity of the applied film may become too high or the applied film may be dried and hardened while the manicure is applied. As a result, forming an uniform film surface may be difficult. On the other hand, if a drying speed of a manicure after applied on a nail is too slow, a proper usability may not be obtained. To balance these two properties the drying time is normally adjusted to be 3 to 8 minutes.

However, more rapid drying time has been required.

A solvent in a manicure applied on a nail is normally removed by a volatilization in the air. But a method to remove a solvent from a manicure applied on a nail by a concentration gradation of the solvent has also been considered. For example, it was disclosed that after a manicure is applied on a nail the applied portion was dipped in water and a solvent in the film formed on the nail was released into water to obtain a rapid drying speed (Japanese Patent Laid Open Shou No. 47-43348).

However this manicure tends to form a whitened film, and it leaves a trace of blushing on a film. Thus it does not satisfy the properties needed for a manicure.

DISCLOSURE OF THE INVENTION

In view of the foregoing problems described above, an object of the present invention is to provide a film composition which is solidified in water of which a painted film is rapidly solidified and also has proper usabilities for use as a manicure. Also, an object of the present invention is to provide a manicure using the composition and a manicuring method.

As a result of diligent studies for obtaining the above-mentioned object, applicants have found that a rapid drying speed and a formation of an uniform film are realized by using specified alkylene glycol ethers and specified ketones as a solvent of a film composition.

A film composition of the present invention which is solidified in water comprises water insoluble film materials, and a solvent which dissolves said water insoluble film materials and soluble with water, wherein said solvent contains one or more solvent ingredients selected from compounds of the following formula (I), formula (II) and formula (III), and characterized by that said film materials are precipitated from the mixture of the remaining solvent and penetrating water in a painted film of the composition when the painted film is dipped in water.

(In the above formula (I), the symbol $R_1$ and $R_2$ means alkyl group of C=1 to 18 or acyl group of C=1 to 18, and the symbol $R_3$ and $R_4$ means H or alkyl group of C=1 to 18, and the symbol m and n means an integral number of 1 to 20.)

(In the above formula (II), the symbol $R_5$ and $R_6$ means alkyl group of C=1 to 18.)

(In the above formula (III), the symbol $R_7$ means alkyl group of C=3 to 18 or acyl group.)

The total amounts of the above-mentioned compounds (I), (II) and (III) in a solvent of the composition of the present invention is preferably more than 50 weight percent per solvent. In this case it is more preferable that the amount of compounds (I) is 15 to 60 weight percent per solvent and the amount of compounds (II) is 30 to 70 weight percent per solvent.

The amounts of the compounds (I) in a solvent of the composition of the present invention is preferably more than 50 weight percent per solvent. In this case it is more preferable that the compounds (II) or (III) is further contained in the solvent.

It is preferable to use more than 50 weight percent per solvent of acetone, methyl ethyl ketone or their mixture and more than 15 weight percent per solvent of solvent ingredients with a boiling point of more than 100° C. which are soluble with acetone, methyl ethyl ketone or their mixture. In this case it is more preferable that the solvent ingredients with a boiling point of more than 100° C. are one or more compounds selected from the compounds (I) or (II) or (III). In this case the compounds (I) are preferably selected from ethylene glycol diethyl ether, ethylene glycol dipropyl ether, ethylene glycol dibutyl ether, ethylene glycol dipentyl ether, diethylene glycol dimethyl ether, diethylene glycol diethyl ether, diethylene glycol dipropyl ether, diethylene glycol dibutyl ether, triethylene glycol dimethyl ether, triethylene glycol diethyl ether, triethylene glycol dipropyl ether, triethylene glycol dibutyl ether. Further the compounds (II) are preferably 3-pentanone, 2-pentanone, 2-methyl-3-pentanone, 3-hexanone, 2-hexanone, 3-methyl-2-pentanone, 4-methyl-2-pentanone. Further the compounds (III) are preferably ethylene glycol monopropyl ether, ethylene glycol monobutyl ether, ethylene glycol monopentyl ether, ethylene glycol monohexyl ether.

A film composition of the present invention is preferably used as a manicure. When the composition is used as a manicure it is characterized by comprising nitrocellulose, sucrose ester resin and organic ester plasticizer as film materials, and 1 to 60 weight percent per the composition of the compounds (I) and 1 to 60 weight percent per the composition of the compounds (II). In this case it is more preferable that the total amount of compounds (I), (II) and (III) is more than 50 weight percent per solvent. In this case it is more preferable that the solvent contains 5 to 40 weight percent per the composition of the compounds (I) and 20 to 60 weight percent per the composition of the compounds (II).

When the composition is used as a manicure its composition is also characterized by comprising nitrocellulose, sulfonamide resin and organic ester plasticizer as film materials, and 1 to 65 weight percent per the composition of the compounds (I) and 1 to 65 weight percent per the composition of the compounds (II). In this case it is more preferable that the total amount of compounds (I), (II) and (III) is more than 50 weight percent per solvent In this case it is more preferable that the solvent contains 10 to 50 weight percent per the composition of the compounds (I) and 15 to 60 weight percent per the composition of the compounds (II).

In a film composition of the present invention a compound of the following formula (IV) can further be contained as a solvent ingredient.

(IV)

(In the above formula (IV), the symbol $R_8$ means alkyl group of C=1 to 18 or acyl group of C=1 to 18, and the symbol $R_9$ and $R_{10}$ means H or alkyl group of C=1 to 18, and the symbol p and q means an integral number of 1 to 20.)

In a film composition of the present invention alcohol or polyhydric alcohol can further be used as a solvent ingredient.

In a film composition of the present invention a compound of the following formula (V) can further be used as a solvent ingredient.

(V)

(In the above formula (V), the symbol $R_{11}$ and $R_{12}$ means alkyl group of C=1 to 18.)

The compounds (I) used as a solvent ingredient of the composition are preferably selected from ethylene glycol dimethyl ether, ethylene glycol diethyl ether, ethylene glycol dipropyl ether, ethylene glycol dibutyl ether, ethylene glycol dipentyl ether, diethylene glycol dimethyl ether, diethylene glycol diethyl ether, diethylene glycol dipropyl ether, diethylene glycol dibutyl ether, triethylene glycol dimethyl ether, triethylene glycol diethyl ether, triethylene glycol dipropyl ether, triethylene glycol dibutyl ether.

The compounds (II) used as a solvent ingredient of the composition are preferably selected from acetone, methyl ethyl ketone, 3-methyl-2-butanone, 3-pentanone, 2-pentanone, 2-methyl-3-pentanone, 3-hexanone, 2-hexanone, 3-methyl-2-pentanone, 4-methyl-2-pentanone.

The compounds (III) used as a solvent ingredient of the composition are preferably selected from ethylene glycol monopropyl ether, ethylene glycol monobutyl ether, ethylene glycol monopentyl ether, ethylene glycol monohexyl ether.

A dual type manicure of the present invention is characterized by that a film formed by applying the manicure on a nail is dried in the air and forms a solidified film between 2 to 10 minutes after the manicure is applied on a nail, and is dried and forms a solidified film for less than 2 minutes by dipping the film in water after the manicure is applied on a nail.

A manicuring method of the present invention is characterized by that a film of the above-described composition applied on a nail is solidified by dipping the applied portion in water after the composition is applied on the nail, and it is more preferable that the film is solidified by dipping in water for less than 2 minutes after painting on a nail.

BEST MODE FOR CARRYING OUT THE INVENTION

Preferable embodiments of the invention will be explained in the following.

Figure 1:
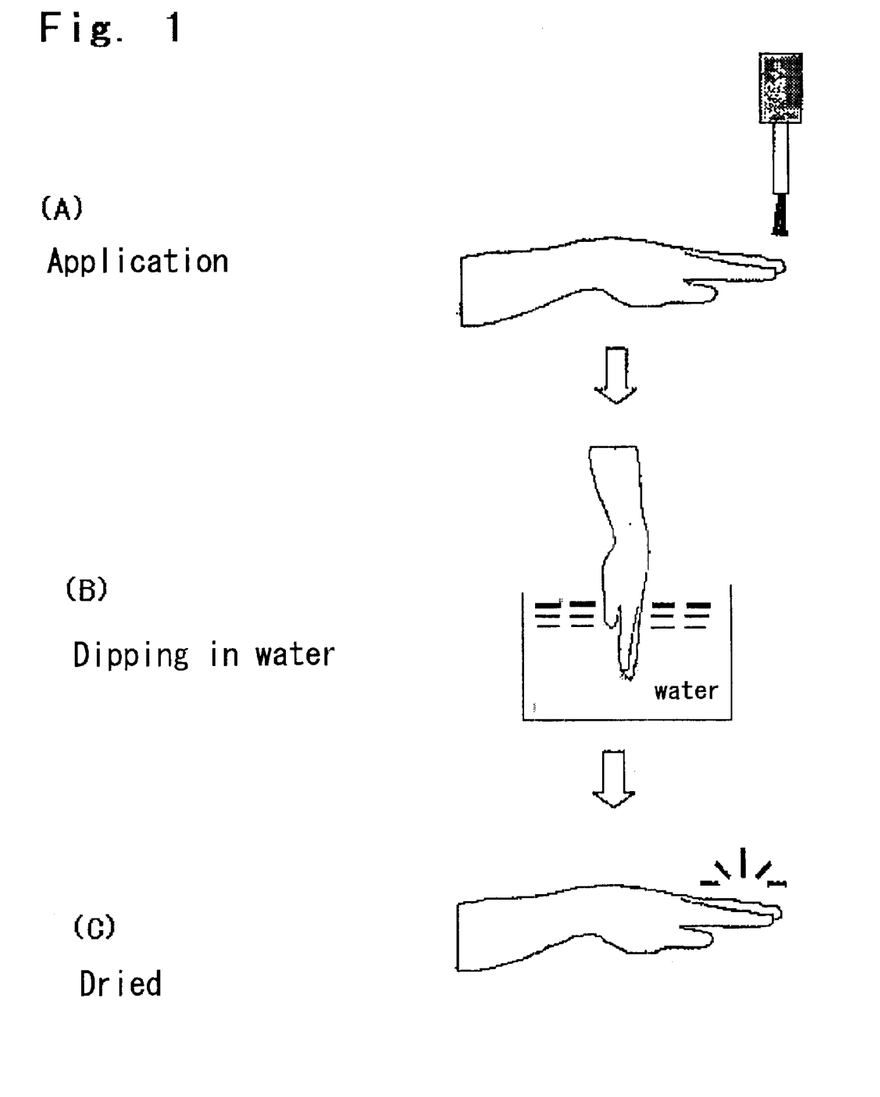
FIG. 1 shows explanatory drawing of use of a film composition of the present invention and the mechanism of film formation.

FIG. 1 illustrates use of a film composition of the present invention and mechanism of film solidification.

A film of the composition can be dried in the air, but when the film is dipped in water after applied on a nail (FIG. 1(A)) more rapid film drying is realized (FIGS. 1(B), (C)). This rapid drying by dipping in water is thought to be caused by the reason that when the film is dipped in water a solvent in the film dissolves into the water and minute amounts of water penetrates into the film. Thus the composition of solvent ingredients in the film would be changed and it promotes a precipitation of the film materials.

Figure 2:
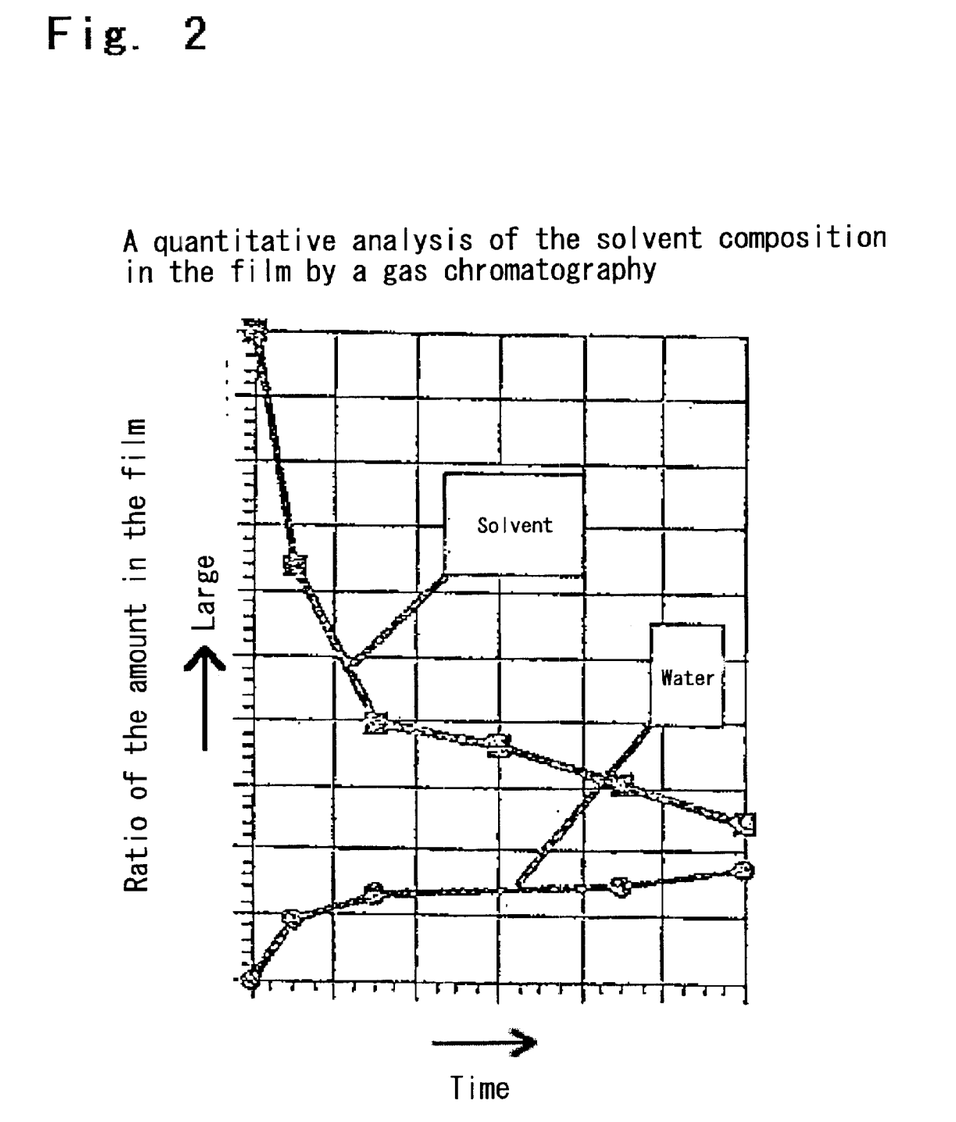
FIG. 2 shows explanatory drawing of a change according to time of a solvent composition in a film formed by applying the composition of the present invention on a nail measured by a gas chromatography when the film is dipped in water.

FIG. 2 illustrates a change according to time of a solvent composition in a film formed by applying the composition of the present invention on a nail measured by a gas chromatography when the film is dipped in water. It is obvious from FIG. 2 that a solvent in the film dissolves into water rapidly and minute amounts of water is simultaneously penetrates into the film. If dipping time is required to be less than 2 minutes for utility it is required that film materials precipitate in a mixed solvent of water and the solvent ingredients of the composition within that time range. On the other hand, when film materials are precipitated in water, the film surface tends to be whitened by some solvent compositions.

In this case manicuring effect may be lost. From these point of view applicants found the compounds (I), (II) and (III) are preferable as solvent ingredients of a film composition of the present invention.

As a solvent ingredient of a film composition of the present invention, compounds of the above-mentioned formula (IV), alcohol, polyhydric alcohol and compounds of the above-mentioned formula (V) can also be contained in addition to the compounds (I) to (II) which are the essential ingredients of the present invention.

In the above-mentioned formula (IV) a carbon number of the alkyl group of the symbol $R_8$, $R_9$, $R_{10}$ is preferably 1 to 10 and the number of the symbol p and q is preferably 1 to 10. The compounds (IV) are preferably selected from ethylene glycol monomethyl ether, ethylene glycol monoethyl ether, ethylene glycol monopropyl ether, ethylene glycol monobutyl ether, diethylene glycol monomethyl ether, diethylene glycol monoethyl ether, diethylene glycol monopropyl ether, diethylene glycol monobutyl ether.

When alcohol or polyhydric alcohol is contained as a solvent ingredient it is preferable to use methanol, ethanol, propanol, isopropanol, butanol, ethylene glycol, diethylene glycol, triethylene glycol, propylene glycol, 1,3-butane diol, hexylene glycol and glycerin. A mixture of these compounds can also be used.

In the above-mentioned formula (V) a carbon number of the alkyl group of the symbol $R_{11}$, $R_{12}$ is preferably 1 to 10, and the compounds (V) are preferably methyl acetate, ethyl acetate, butyl acetate, isopropyl acetate, methyl propionate, ethyl propionate, butyl propionate, isopropyl propionate, or these derivatives which have branch carbon chain in there alkyl group, or have substituents such as —OR, —COOR, —SO$_3$R. A mixture of these compounds can also be used.

A carbon number of the alkyl group of the symbol $R_1$, $R_2$, $R_3$, $R_4$ of the compounds (I) is preferably 1 to 10, and the number of the symbol m and n are preferably 1 to 10. The compounds (I) are preferably selected from ethylene glycol dimethyl ether, ethylene glycol diethyl ether, ethylene glycol dipropyl ether, ethylene glycol dibutyl ether, ethylene glycol dipentyl ether, diethylene glycol dimethyl ether, diethylene glycol diethyl ether, diethylene glycol dipropyl ether, diethylene glycol dibutyl ether, triethylene glycol dimethyl ether, triethylene glycol diethyl ether, triethylene glycol dipropyl ether, triethylene glycol dibutyl ether.

A carbon number of the alkyl group of the symbol $R_5$, $R_6$ of the compounds (II) is preferably 1 to 6, and the compounds (II) are preferably selected from acetone, methyl ethyl ketone, 3-methyl-2-butanone, 3-pentanone, 2-pentanone, 2-methyl-3-pentanone, 3-hexanone, 2-hexanone, 3-methyl-2-pentanone, 4-methyl-2-pentanone.

A carbon number of the alkyl group of the symbol $R_7$ of the compounds (III) is preferably 1 to 10, and the compounds (III) are preferably selected from ethylene glycol monopropyl ether, ethylene glycol monobutyl ether, ethylene glycol monopentyl ether, ethylene glycol monohexyl ether.

The derivatives of the compounds (I) to (V) which have branch carbon chain in there alkyl group, or have substituents such as —OR, —COOR, —SO$_3$R also may be used.

A manicure which used a film composition of the present invention forms a solidified film on a nail after the manicure is applied on the nail by dipping the applied portion in water (warm water is also applicable) and precipitating the film materials. In this case the drying (solidifying) time is less than 2 minutes.

The film formed by applying the manicure on a nail can also be dried in the air as well as a normal manicure though the drying time is longer than the case in which the film is dipped in water.

In a film composition of the present invention film forming ingredients normally use, resins, plasticizers are used. And organic modified cray, pigments, thickening agents, perfumes, moisturizing agents, oil ingredients, medical ingredients, water soluble ingredients can be contained in the range of the object of the present invention.

As film forming ingredients, for example, Nitrocellulose ½, Nitrocellulose ¼, Nitrocellulose ⅛, Nitrocellulose 1/16 can be used in a film composition of the present invention.

As resins, for example, alkyd resin, acrylic resin, acrylic silicone resin, polyester resin, sucrose resin, sulfonamide resin, rosin, phenolic resin, amino resin, epoxy resin can be used.

As plasticizers, for example, dibutyl phthalate, dioctyl phthalate, tributyl citrate, acetyl tributyl citrate, acetyl triethyl citrate, camphor can be used.

When a film composition of the present invention is used as a manicure, it is preferable that the amount of said film forming ingredients is 5 to 40 weight percent per the composition and sucrose ester resin or sulfonamide resin is contained with organic ester plasticizer. In this case it is preferable that a part or all of hydroxyl groups in sucrose resin are esterified by compounds of the following formula (VI).

(VI)

(In the above formula (VI), the symbol $R_{13}$ means alkyl group of C=1 to 10. This alkyl group can have a phenyl group or the other function groups.)

For example sucrose acetate resin such as sucrose acetate isobutylate and sucrose benzoate resin such as sucrose benzoate are preferable, and it is preferable that these sucrose ester resins are used in the range 2 to 20 weight percent per the composition.

On the other hand, As sulfonamide resin, for example, it is preferable to be toluenesulfonamide/epoxy resin and toluenesulfonamide/formaldehyde resin, and it is preferable that these sulfonamide resins are used in the range 2 to 20 weight percent per the composition.

Organic ester plasticizers used with these resins are preferably citrate such as tributyl citrate, acetyl tributyl citrate and acetyl triethyl citrate; phthalate such as dimethyl phthalate, diethyl phthalate, dipropyl phthalate, dibutyl phthalate, and it is preferable that such organic ester plasticizers are used in the range 2 to 20 weight percent per the composition.

As pigment and other powders, inorganic powder such as talc, kaolin, sericite, muscovite, synthetic mica, phlogopite, red mica, black mica, lichia mica, vermiculite, magnesium carbonate, calcium carbonate, diatomaceous earth, magnesium silicate, calsium silicate, aluminium silicate, barium silicate, barium sulfate, strontium silicate, metal tungstate, silica, hydroxyapatite, zeolite, boron nitrate, ceramics powder; organic powder such as nylon powder, polyethylene powder, benzoguanamine powder, ethylene fluoride powder, styrene-divinylbenzene copolymer powder, distyrenebenzene pinhole polymer powder, microcrystalline cellulose; inorganic white pigment such as titanium oxide, zinc oxide; inorganic red pigment such as red iron oxide, iron titanate; inorganic brown pigment such as maghemite; inorganic yellow pigment such as yellow iron oxide, yellow ocher; inorganic black pigment such as black iron oxide, carbon black; inorganic purple pigment such as mango violet, cobalt violet; inorganic green pigment such as chromium oxide, chromium hydroxide, cobalt titanate; inorganic blue pigment such as ultramarine, iron blue; nacreous pigment such as titanium oxide coated bismuth oxychloride, bismuth oxychloride, titanium oxide coated talc, fish scale flake, colored titanium oxide coated mica; clay such as bentonite; metallic powder such as aluminium powder, copper powder, organic pigment such as Lithol Rubine B (D & C Red No.6), Lithol Rubine BCA (D & C Red No.7), Lake Red CBA (D & C Red No.9), Lithol Red (D & C Red No.10), Deep Maroon (D & C Red No.34), Helindone Pink CN (D & C Red No.30), Permaton Red, Parmanent Red F5R, Permanent Orange (I) & C Orange No.17), Benzidine Orange G, Benzidine Yellow G, Hanza Yellow (EXT. D & C Yellow No.5), Phthalocyanine Blue; organic pigment of zirconium, barium, aluminum lake, or the like such as Erythrosine (FD & C Red No.3), Phloxine B (D & C Red No.28), Acid Red, Fast Acid Magenta (D & C Red No.33), Eosine YS (D & C Red No.22), Eosine YSK, Violamine R (EXT. D & C Red No.3), Oil Red XO, Orange II (D & C Orange No.4), Tartrazine (FD & C Yellow No.5), Sunset Yellow FCF (FD & C Yellow No.6), Uranine K, Quinoline Yellow WS (D & C Yellow No.10), Fast Green FCF (FD & C Green No.3), Brilliant Blue FCF (FD & C Blue No.1); natural dye such as chlorophyll, beta carotene; magnesium oxide, magnesium hydroxide, calcium oxide, calcium hydroxide, aluminium oxide, aluminium hydroxide, silica, iron hydroxide, titanium dioxide, titanium oxide, zirconium oxide, chromium oxide, manganese oxide, cobalt oxide, nickel oxide, iron titanate, cobalt titanate can be used. One or more compounds selected from these arc used.

As a thickening agent, organic clay such as Benton 27, Benton 38, polymer such as acrylic polymer, polysaccharide, carboxyvinylpolymer or the like may be used.

A film composition forming a solidified film by dipping in water of the present invention is applicable to paints, car wax, a method to form a thin film, and so on. In addition to these applications, it is applicable to cosmetics, such as a body paint, a pack, a poultice, a nail art pen, and so on.

In the following, the present invention will be explained in detail based on the embodiments of the present invention. However, the present invention should not be restricted thereto. Unless otherwise stated, quantities are expressed as weight percent. When nitrocellulose is used in the following, nitrocellulose is used as isopropyl alcohol solution of 30 weight percent.

Evaluation Methods

Before explanation of embodiments, the evaluation methods are explained.

The Drying Time

A sample was applied on a nail with brushing the nail once and then the nail was dipped in water for a suitable time. Then the film formed on the nail by applying the sample was touched with a fingertip and it was judged whether a fingerprint was formed on the film or not. The dipping time (the drying time) in water between the time just after the sample was applied on the nail and the time when a fingerprint was no longer formed by touching of the surface of the film was evaluated based on the following evaluation standard.

The Symbol ○: The drying time was shorter than 2 minutes.
The Symbol Δ: The drying time was 2 to 5 minutes.
The Symbol ×: The drying time was longer than 5 minutes.

Ease of Application on a Nail

Each sample was filled in a 10 ml glass bottle equipped with an application brush. Then ease of application on a nail was evaluated based on the following evaluation standard.

The Symbol ○: Good (The feeling of application was smooth and it was easy to finely apply on a nail.)
The Symbol Δ: little Bad (The application was a little difficult.)
The Symbol ×: Bad (T he application was difficult.)

Uniformity of a Film Surface

A sample was applied on a nail with brushing the nail once and the film formed on the nail by applying the sample was dipped in water. Then a surface appearance of the solidified film was evaluated based on the following evaluation standard.

The Symbol ○: Good (The surface of the film was fine and smooth.)
The Symbol Δ: A little Bad (The surface appearance of the film was a little cloudy.)
The Symbol ×: Bad (The film surface was whitened.)

A. Selection of a Solvent

At first film forming properties in water of samples containing different solvents were investigated. The results are shown in Table 1 and Table 2.

TABLE 1

| | Sample | | | |
|---|---|---|---|---|
| Ingredients | 1 | 2 | 3 | 4 |
| Nitrocellulose | 15.0 | 15.0 | 15.0 | 15.0 |
| Ethylene glycol diethyl ether | 85.0 | | | |
| Diethylene glycol diethyl ether | | 85.0 | | |
| Acetone | | | 85.0 | |
| Methyl ethyl ketone | | | | 85.0 |
| The DryingTime | ○ | ○ | ○ | ○ |
| Ease of Application | ○ | ○ | Δ | ○~Δ |
| Uniformity of a Film Surface | ○ | ○ | ○ | ○ |

TABLE 2

| | Sample | | | |
|---|---|---|---|---|
| Ingredients | 5 | 6 | 7 | 8 |
| Nitrocellulose | 15.0 | 15.0 | 15.0 | 15.0 |
| Ethylene glycol monobutyl ether | 85.0 | | | |
| Ethylene glycol monoethyl ether | | 85.0 | | 42.5 |
| Butyl acetate | | | 85.0 | |
| Modified alcohol | | | | 42.5 |
| The Drying Time | ○ | ○ | × | ○ |
| Ease of Application | ○ | ○ | ○ | ○ |
| Uniformity of a Film Surface | ○ | × | — | × |

It is recognized from Table 1 and Table 2 that when alkylene glycol ethers or ketones of the above-described compounds (I) such as ethylene glycol diethyl ether, diethylene glycol diethyl ether, or the above-described compounds (II) such as acetone and methyl ethyl ketone, or the above-described compounds (III) such as ethylene glycol monobutyl ether were used as a solvent the drying speed of the painted film was rapid and an uniform film with no whitening was obtained.

On the other band, when butyl acetate, which has been commonly used as a solvent of a manicure, was used as a solvent a film was not dried by dipping in water. When ethylene glycol monoethyl ether and modified alcohol were used as a solvent as well as prior art, though film drying was performed, a the film was whitened and an appearance of the film lacked uniformity.

Next, combinations of the above-described useful solvents, and compounds related to the above-described useful solvents were examined. The results are shown in Table 3.

TABLE 3

| Ingredients | Sample 9 | 10 | 11 | 12 | 13 |
|---|---|---|---|---|---|
| Nitrocellulose | 15.0 | 15.0 | 15.0 | 15.0 | |
| Ethylene glycol monobutyl ether | 42.5 | 42.5 | | | |
| Diethylene glycol diethyl ether | 42.5 | | 42.5 | | |
| Acetone | | 21.25 | 21.25 | | |
| Methyl ethyl ketone | | 21.25 | 21.25 | | |
| Ethylene glycol dibutyl ether | | | | 85.0 | |
| Triethylene glycol dimethyl ether | | | | | 85.0 |
| The Drying Time | ○ | ○ | ○ | ○ | ○ |
| Ease of Application | ○ | ○ | ○ | ○ | ○ |
| Uniformity of a Film Surface | ○ | ○ | ○ | ○ | ○ |

It is recognized from Table 3 that if the compounds (I), (II) and (III) were used as solvent ingredients rapid drying and an uniformity of a film surface was obtained. And when a mixture of these compounds were used, good film properties were also obtained.

Next, combinations of the essential solvent ingredients of the present invention and a solvent generally used for a manicure were investigated. The results are shown in Table 4.

TABLE 4

| Ingredients | Sample 14 | 15 | 16 | 17 | 18 |
|---|---|---|---|---|---|
| Nitrocellulose | 15.0 | 15.0 | 15.0 | 15.0 | 15.0 |
| Diethylene glycol diethyl ether (DEGDEE) | 85.0 | 59.5 | 42.5 | 25.5 | 0 |
| Butyl acetate | 0 | 25.5 | 42.5 | 59.5 | 85.0 |
| DEGDEE/(DEGDEE + Butyl acetate) | 100 percent | 70 | 50 | 30 | 0 |
| The Drying Time | ○ | ○ | ○ | Δ | × |
| Ease of Application | ○ | ○ | ○ | ○ | ○ |
| Uniformity of a Film Surface | ○ | ○ | ○ | × | — |

In Table 4 butyl acetate, which is a generally used solvent for a manicure, was mixed with diethylene glycol diethyl ether, which is one of the essential solvent ingredients of the present invention. From Table 4 it is recognized that sufficient film properties were maintained when the amount of butyl acetate was less tan 50 weight percent per solvent. On the other hand, when the amount of butyl acetate exceeded 50 weight percent per solvent the film properties became worse.

[Durability]

A sample was applied on a nail of each 10 women panels. Then the applied portion was dipped in water to form a dried film. A degree of peeling of the film was observed after four days past, and it was evaluated as points according to the following standard.

| | |
|---|---|
| Good durability | 3 points |
| Normal durability | 2 points |
| A little bad Durability | 1 point |
| Bad durability | 0 point |

Then the points evaluated by 10 panels according to the standard was averaged and rounded to one decimal. Then the average was evaluated according to the following standard.
The Evaluation Standard of Durability
◎: The average was more than 2.5 points.
○: The average was 2 to 2.4 points.
Δ: The average was 1 to 1.9 points.
×: The average was smaller than 1 points.
The results are shown in Table 5.

TABLE 5

| Ingredients | Sample 19 | 20 | 21 | 22 | 23 | 24 |
|---|---|---|---|---|---|---|
| Nitrocellulose | 10 | 10 | 10 | 10 | 10 | 10 |
| Resin | 5 | 5 | 5 | 5 | 5 | 5 |
| Plasticizer | 5 | 5 | 5 | 5 | 5 | 5 |
| DEGDEE | 8 | 12 | 24 | 36 | 48 | 52 |
| Acetone | 60 | 56 | 48 | 32 | 24 | 20 |
| Butyl acetate | 12 | 12 | 8 | 12 | 8 | 8 |
| DEGDEE/Total Solvent (weight percent) | 10 | 15 | 30 | 45 | 60 | 65 |
| Acetone/Total Solvent (weight percent) | 75 | 70 | 60 | 45 | 30 | 25 |
| Durability | ○ | ◎ | ◎ | ◎ | ◎ | ○ |
| The Drying Time | ○ | ○ | ○ | ○ | ○ | ○ |
| Ease of Application | ○ | ○ | ○ | ○ | ○ | ○ |
| Uniformity of a Film Surface | ○ | ○ | ○ | ○ | ○ | ○ |

DEGDEE: Diethylene glycol diethyl ether

It is recognized from Table 5 that when a combination amount of diethylene glycol diethyl ether, which is one of the compounds (I), is 15 to 60 weight percent per solvent and a combination amount acetone, which is one of the compound (II), is 30 to 70 weight percent per solvent the durability is very good.

On the other hand, when a combination amount of diethylene glycol diethyl ether and acetone is outside the above-mentioned range the durability is inferior to that of the above-mentioned condition.

Next, the durability of samples using a solvent consisting of alkylene glycol ethers of the compounds (I) and (III) were examined. The results are shown in Table 6.

TABLE 6

| Ingredients | Sample 25 | 26 | 27 | 28 |
|---|---|---|---|---|
| Nitrocellulose | 15.0 | 15.0 | 15.0 | 15.0 |
| Resin | 5.0 | 5.0 | 5.0 | 5.0 |
| Plasticizer | 5.0 | 5.0 | 5.0 | 5.0 |
| Ethylene glycol diethyl ether | 75.0 | | | |
| Diethylene glycol diethyl ether | | 75.0 | | |
| Triethylene glycol dimethyl ether | | | 75.0 | |
| Ethylene glycol monobutyl ether | | | | 75.0 |
| Durability | ◎ | ◎ | ◎ | ○ |

It is recognized from Table 6 that when alkylene glycol diethers such as ethylene glycol diethyl ether or diethylene glycol diethyl ether are used the durability is very good.

On the other hand, when alkylene glycol monoethers such as ethylene glycol monobutyl ether are used the durability is inferior to very good results of alkylene glycol diethers.

Next, combinations of the compounds (I) and a solvent generally used for a manicure were investigated. The results are shown in Table 7.

TABLE 7

| Ingredients | Sample | | | | |
|---|---|---|---|---|---|
| | 29 | 30 | 31 | 32 | 33 |
| Nitrocellulose | 15.0 | 15.0 | 15.0 | 15.0 | 15.0 |
| Resin | 5.0 | 5.0 | 5.0 | 5.0 | 5.0 |
| Plasticizer | 5.0 | 5.0 | 5.0 | 5.0 | 5.0 |
| Diethylene glycol diethyl ether (DEGDEE) | 75.0 | 52.5 | 37.5 | 22.5 | 0 |
| Butyl acetate | 0 | 22.5 | 37.5 | 52.5 | 75.0 |
| DEGDEE/ (DEGDEE + Butyl acetate) | 100 percent | 70 | 50 | 30 | 0 |
| Durability | ◎ | ○ | ○ | — | — |

In Table 7 butyl acetate, which is a generally used solvent for a manicure, was mixed with diethylene glycol diethyl ether of the compounds (I). From Table 7 it is recognized that sufficient durability was maintained when the amount of butyl acetate was less than 50 weight percent per solvent On the other hand, when the amount of butyl acetate exceeded 50 weight percent per solvent the durability became worse.

Next, combinations of the compounds (I) as a main solvent ingredient and other solvent ingredients consisting of the compounds (II) and (III) were investigated. The results are shown in Table 8.

TABLE 8

| Ingredients | Sample | | | | | |
|---|---|---|---|---|---|---|
| | 34 | 35 | 36 | 37 | 38 | 39 |
| Nitrocellulose | 15.0 | 15.0 | 15.0 | 15.0 | 15.0 | 15.0 |
| Resin | 5.0 | 5.0 | 5.0 | 5.0 | 5.0 | 5.0 |
| Plasticizer | 5.0 | 5.0 | 5.0 | 5.0 | 5.0 | 5.0 |
| Diethylene glycol diethyl ether (DEGDEE) | 45.0 | 45.0 | 45.0 | 37.5 | 37.5 | 37.5 |
| Acetone | 30.0 | — | — | 37.5 | — | — |
| Ethylene glycol monobutyl ether | — | 30.0 | — | — | 37.5 | — |
| Butyl acetate | — | — | 30.0 | — | — | 37.5 |
| DEGDEE/(Total solvent) | 60 percent | 60 | 60 | 50 | 50 | 50 |
| Durability | ◎ | ◎ | ○ | ◎ | ◎ | ○ |
| The DryingTime | ○ | ○ | ○ | ○ | ○ | ○ |
| Ease of Application | ○ | ○ | ○ | ○ | ○ | ○ |
| Uniformity of a Film Surface | ○ | ○ | ○ | ○ | ○ | ○ |

It is recognized from Table 8 that when diethylene glycol diethylether, which is one of the compound (I), was mixed with acetone, which is one of the compound (II), or ethylene glycol monobutyl ether, which is one of the compounds (III), and the mixture was used as a solvent, the durability is more superior to the case where butyl acetate, which is generally used as a solvent of manicure, was mixed with diethylene glycol diethylether and used the mixture as a solvent.

Next, the case where acetone and methylethylketone were used as main solvent ingredients was examined. In this case the evaluation shown in the following was also conducted.
Fine Finish A sample was applied on a nail of each women panels. The applied portion was dried by dipping the nail in water. An appearance of the solidified film on the nail was observed and evaluated according to the following standard.
◎: The finish was fine and no trace of brush was observed. Fine finish was obtained for all of the cases.
○: The finish was fine and traces of brush were little observed. Fine finish was obtained for most of the cases.
Δ: Traces of brush were observed for some cases.
×: Fine finish was not obtained for most of the cases.
The results are shown in Table 9 and Table 10.

TABLE 9

| Ingredients | Sample | | | | | | |
|---|---|---|---|---|---|---|---|
| | 40 | 41 | 42 | 43 | 44 | 45 | 46 |
| Nitrocellulose | 20 | 20 | 20 | 20 | 20 | 20 | 20 |
| Acetone | 80 | 48 | 48 | 48 | 48 | 48 | 48 |
| 3-Methyl-2-butanone (b.p. 94 to 95° C.) | | 32 | | | | | |
| 2-Pentanone (b.p. 100 to 110° C.) | | | 32 | | | | |
| 4-Methyl-2-pentanone (b.p. 117 to 118° C.) | | | | 32 | | | |
| 2-Hexanone (b.p. 127° C.) | | | | | 32 | | |
| DEGDEE (b.p. 188° C.) | | | | | | 32 | |
| EGMBE (b.p. 171 to 172° C.) | | | | | | | 32 |
| Acetone/Total solvent (weight percent) | 100 | 60 | 60 | 60 | 60 | 60 | 60 |
| The DryingTime | ○ | ○ | ○ | ○ | ○ | ○ | ○ |
| Uniformity of a Film Surface | ○ | ○ | ○ | ○ | ○ | ○ | ○ |
| Ease of Application | Δ | ○~Δ | ○ | ○ | ○ | ○ | ○ |
| Fine Finish | Δ | ○~Δ | ◎ | ◎ | ◎ | ◎ | ◎ |

DEGDEE: Diethylene glycol diethyl ether
EGMBE: Ethylene glycol monobutyl ether

From Table 9 it is recognized that when a compound which has b.p. (boiling point) of more than 100° was mixed with acetone as a solvent ingredient the good drying speed and uniform film surface with no whitening were obtained. Further, Application was easy and finish of the applied nail was fine.

On the other hand, when only acetone or a mixture of acetone and a relatively volatile compound (b.p. of less than 100° C.) was used as a solvent, application was difficult because of fast volatilization of acetone. And traces of brush remained on the film surface. Thus fine finish was not sufficiently obtained.

TABLE 10

| Ingredients | Sample | | | | | | |
|---|---|---|---|---|---|---|---|
| | 47 | 48 | 49 | 50 | 51 | 52 | 53 |
| Nitrocellulose | 20 | 20 | 20 | 20 | 20 | 20 | 20 |
| Methyl ethyl ketone | 80 | 48 | 48 | 48 | 48 | 48 | 48 |
| 3-Methyl-2-butanone (b.p. 94 to 95° C.) | | 32 | | | | | |
| 2-Pentanone (b.p. 100 to 110° C.) | | | 32 | | | | |
| 4-Methyl-2-pentanone (b.p. 117 to 118° C.) | | | | 32 | | | |
| 2-Hexanone (b.p. 127° C.) | | | | | 32 | | |
| DEGDEE (b.p. 188° C.) | | | | | | 32 | |
| EGMBE (b.p. 171 to 172° C.) | | | | | | | 32 |
| Methyl ethyl ketone/Total solvent (weight percent) | 100 | 60 | 60 | 60 | 60 | 60 | 60 |
| The Drying Time | ○ | ○ | ○ | ○ | ○ | ○ | ○ |
| Uniformity of a Film Surface | ○ | ○ | ○ | ○ | ○ | ○ | ○ |
| Ease of Application | ○~Δ | ○ | ○ | ○ | ○ | ○ | ○ |
| Fine Finish | ○~Δ | ○ | ◎ | ◎ | ◎ | ◎ | ◎ |

DEGDEE: Diethylene glycol diethyl ether
EGMBE: Ethylene glycol monobutyl ether

From Table 10 it is recognized that when a compound which has b.p. (boiling point) of more than 100° C. was mixed with methyl ethyl ketone as a solvent ingredient good drying speed and uniform film surface with no whitening were obtained. Further, application was easy and finish of the applied nail was fine.

On the other hand, when only methyl ethyl ketone or a mixture of methyl ethyl ketone and a relatively volatile compound (b.p. of less than 100° C.) was used as a solvent, application was difficult because of fast volatilization of methyl ethyl ketone. And traces of brush remained on the film surface. Thus fine finish was not sufficiently obtained.

Next, the relationships between combination amount of a compound which has b.p. of more than 100° C. in a solvent of a sample, and ease of application and fine finish were examined. The results are shown in Table 11 and Table 12.

TABLE 11

| Ingredients | Sample | | | |
|---|---|---|---|---|
| | 54 | 55 | 56 | 57 |
| Nitrocellulose | 20 | 20 | 20 | 20 |
| Acetone | 72 | 68 | 64 | 48 |
| 4-Methyl-2-pentanone (4M2PN) | 8 | 12 | 16 | 32 |
| 4M2PN/Total solvent (weight percent) | 10 | 15 | 20 | 40 |
| Ease of Application | Δ | ◯ | ◯ | ◯ |
| Fine Finish | ◯ | ◉ | ◉ | ◉ |
| The DryingTime | ◯ | ◯ | ◯ | ◯ |
| Uniformity of a Film Surface | ◯ | ◯ | ◯ | ◯ |

It is recognized from the results in Table 11 that when the combination amount of a compound which has b.p. of more than 100° C. (4-methyl-2-pentanone: b.p. of 117 to 118° C.) in the solvent was more than 15 weight percent per solvent good drying speed and uniform film surface with no whitening were obtained. Further, application was easy and finish of the applied nail was fine.

On the other hand, when the combination amount of 4-methyl-2-pentanone was less than 15 weight percent per solvent, application was not necessarily easy and finish of the applied nail was not sufficiently fine.

TABLE 12

| Ingredients | Sample | | | |
|---|---|---|---|---|
| | 58 | 59 | 60 | 61 |
| Nitrocellulose | 20 | 20 | 20 | 20 |
| Methyl ethyl ketone | 72 | 68 | 64 | 48 |
| 2-Hexanone | 8 | 12 | 16 | 32 |
| 2-Hexanon/Total solvent (weight percent) | 10 | 15 | 20 | 40 |
| Ease of Application | ◯~Δ | ◯ | ◯ | ◯ |
| Fine Finish | ◯ | ◉ | ◉ | ◉ |
| The Drying Time | ◯ | ◯ | ◯ | ◯ |
| Uniformity of a Film Surface | ◯ | ◯ | ◯ | ◯ |

It is recognized from the results in Table 12 that when the combination amount of a compound which has b.p. of more than 100° C. (2-hexanone: b.p. of 127° C.) in the solvent was more than 15 weight percent per solvent good drying speed and uniform film surface with no whitening were obtained. Further, application was easy and finish of the applied nail was fine.

On the other band, when the combination amount of 2-hexanone was less than 15 weight percent per solvent, application was not necessarily easy and finish of the applied nail was not sufficiently fine.

Further the film properties were examined for samples which use the compounds (II) and (III) with a boiling point of more than 100° C. as solvent ingredients. The results are shown in Table 13.

TABLE 13

| Ingredients | Sample | | | |
|---|---|---|---|---|
| | 62 | 63 | 64 | 65 |
| Nitrocellulose | 15.0 | 15.0 | 15.0 | 15.0 |
| Sulfonamide resin | 7.0 | 7.0 | 7.0 | 7.0 |
| Citrate | 4.0 | 4.0 | 4.0 | 4.0 |
| Acetone | 50.0 | 50.0 | 40.0 | 50.0 |
| MEK | — | — | 17.5 | — |
| DEGDEE | 20.0 | — | 12.5 | — |
| TEGDME | — | 20.0 | — | — |
| DEGDBE | — | — | — | 20.0 |
| Cororants | 4.0 | 4.0 | 4.0 | 4.0 |
| The Drying Time | ◯ | ◯ | ◯ | ◯ |
| Ease of Application | ◯ | ◯ | ◯ | ◯ |
| Uniformity of a Film Surface | ◯ | ◯ | ◯ | ◯ |
| Fine Finish | ◉ | ◉ | ◉ | ◉ |

MEK: Methyl ethyl ketone
DEGDEE: Diethylene glycol diethyl ether
TEGDME: Triethylene glycol dimethyl ether
DEGDBE: Diethylene glycol dibutyl ether It is recognized from Table 13 that the samples which use the compounds (II), (III) with a boiling point of more than 100° C. showed good properties.

B. Preferable Compositions When Used as a Manicure

To obtain more preferable film properties for use as a manicure further investigation was done about a resin and a composition of a solvent of samples. In the following the new evaluation standards were used for the in detail evaluation of ease of application and an uniformity of a film surface to investigate more preferable compositions for use as a manicure. The new evaluation standards are as follows. The evaluation standards of the dying time in the following are the same as the above-described evaluation standards.

Ease of Application on a Nail

The new evaluation standard is as follows.

Each sample was filled in a 10 ml glass bottle equipped with an application brush. Then ease of application on a nail was evaluated based on the following evaluation standard.

The Symbol ◉: Very Good (The feeling of application was smooth and it was easy to finely apply on a nail.)

The Symbol ◯: Good

The Symbol Δ: A little Bad (The application was a little difficult.)

The Symbol ×: Bad (The application was difficult.)

Uniformity of a Film Surface

A sample was applied on a nail with brushing the nail once and the film formed on the nail by applying the sample was dipped in water. Then a surface appearance of the solidified film was evaluated based on the following evaluation standard.

The Symbol ◉: Very Good (The surface of the film was fine and smooth.)

The Symbol ◯: Good

The Symbol Δ: A little Bad (The surface appearance of the film was a little cloudy.)

The Symbol ×: Bad (The film surface was whitened.)

At first, sucrose ester resin was selected and samples containing sucrose resin were examined in the following.

Film properties of each samples with different solvent were examined. The results are shown in Table 14.

TABLE 14

| Ingredients | Sample 66 | 67 | 68 |
|---|---|---|---|
| Nitrocellulose | 20.0 | 20.0 | 20.0 |
| Sucrose ester resin | 8.0 | 8.0 | 8.0 |
| Citrate | 8.0 | 8.0 | 8.0 |
| Diethylene glycol diethyl ether | 25.0 | — | — |
| Acetone | 35.0 | — | — |
| Ethylene glycol monoethyl ether | — | 60.0 | — |
| Butyl acetate | — | — | 60.0 |
| Cororants | 4.0 | 4.0 | 4.0 |
| The Drying Time | ○ | ○ | X |
| Ease of Application | ◎ | ◎ | ◎ |
| Uniformity of a Film Surface | ◎ | X | — |

It is recognized from Table 14 that when a mixture of diethylene glycol diethyl ether, which is one of the compounds (I), and acetone, which is one of the compounds (II) was used as a solvent the drying speed in water was rapid and fine film surface with no whitening was obtained.

On the other band, when butyl acetate, which has been commonly used as a solvent of a manicure, was used as a solvent the film was not dried by dipping in water. When ethylene glycol monoethylether was used as well as the prior art, though film drying was performed, the film surface was whitened and an appearance of the film lacked uniformity.

Further film properties of samples containing a solvent consisting of the compounds (I) and the compounds (II) were examined. The results are shown in Table 15.

TABLE 15

| Ingredients | Sample 69 | 70 | 71 | 72 | 73 | 74 |
|---|---|---|---|---|---|---|
| Nitrocellulose | 20.0 | 20.0 | 20.0 | 20.0 | 20.0 | 20.0 |
| Sucrose ester resin | 8.0 | 8.0 | 8.0 | 8.0 | 8.0 | 8.0 |
| Citrate | 8.0 | 8.0 | 8.0 | 8.0 | 8.0 | 8.0 |
| Diethylene glycol diethyl ether | 25.0 | — | — | 25.0 | 25.0 | — |
| Ethylene glycol dibutyl ether | — | 25.0 | — | — | — | 25.0 |
| Triethylene glycol dimethyl ether | — | — | 25.0 | — | — | — |
| Acetone | 35.0 | 35.0 | 35.0 | — | 17.5 | — |
| Methyl ethyl ketone | — | — | — | 35.0 | 17.5 | 35.0 |
| Cororants | 4.0 | 4.0 | 4.0 | 4.0 | 4.0 | 4.0 |
| The Drying Time | ○ | ○ | ○ | ○ | ○ | ○ |
| Ease of Application | ◎ | ◎ | ◎ | ◎ | ◎ | ◎ |
| Uniformity of a Film Surface | ◎ | ◎ | ◎ | ◎ | ◎ | ◎ |

It is recognized from Table 15 that, when a mixture of the compounds (I) and the compounds (II) was used as a solvent, the drying speed in water was rapid and fine film surface was obtained.

Next, the samples which use resins of the following (1) to (5) as one of the film materials were evaluated. Further, adhesion to a nail, which is one of the important properties for manicure, was also evaluated according to the following procedure. The results are shown in Table 16.
Resin (1) Sucrose Acetate Isobutylate (Sucrose ester resin)
Resin (2) Sucrose benzoate (Sucrose ester resin)
Resin (3) Phthalic acid/Glycerin/Glycidyl Versatate (Alkyd resin)
Resin (4) Alkyl Acrylate/Alkyl Methacrylate Copolymer (Acrylic resin)
Resin (5) Methacrylic acid/Acrylic acid 12-Hydroxyethyl Methacrylate Copolymer (Acrylic resin)
The Adhesion Test
A sample was extended onto a glass board by an applicator, and a film of the sample with a constant thickness formed on the glass board was dried by dipping in water. Then the film was separated to 100 square sections. These sections were made according to the procedure in which the film was mechanically scratched by a sharpened needle to give 11 linear traces and the other 11 linear traces crossed at right angles to said 11 linear traces to form 100 separated square sections (1 mm×1 mm). Then the adhesion to a nail was evaluated according to the following evaluation standard in consideration of the ratio of the number of the remained square film sections on the glass board. Namely, A higher number of the remained square film sections on the glass board means better adhesion to a nail (Peeling off the film from a nail is relatively difficult). On the other hand, a lower number of the remained square film sections on the glass board means worse adhesion to a nail (Peeling off the film from a nail is relatively easy).

The evaluation Standard

The symbol ◎: A ratio of a number of remained square films on the glass board was more than 80 percent.

The symbol ○: A ratio of a number of remained square films on the glass board was more than 60 percent and smaller than 80 percent.

The symbol Δ: A ratio of a number of remained square films on the glass board was more than 40 percent and smaller than 60 percent.

The symbol x: A ratio of a number of remained square films on the glass board was more than 40 percent.

TABLE 16

| Ingredients | Sample 75 | 76 | 77 | 78 | 79 |
|---|---|---|---|---|---|
| Nitrocellulose | 20.0 | 20.0 | 20.0 | 20.0 | 20.0 |
| Resin (1) | 8.0 | | | | |
| Resin (2) | | 8.0 | | | |
| Resin (3) | | | 8.0 | | |
| Resin (4) | | | | 8.0 | |
| Resin (5) | | | | | 8.0 |
| Citrate | 8.0 | 8.0 | 8.0 | 8.0 | 8.0 |
| Diethylene glycol diethyl ether | 25.0 | 25.0 | 25.0 | 25.0 | 25.0 |
| Acetone | 35.0 | 35.0 | 35.0 | 35.0 | 35.0 |
| Cororants | 4.0 | 4.0 | 4.0 | 4.0 | 4.0 |
| The Drying Time | ○ | ○ | ○ | ○ | ○ |
| Ease of Application | ◎ | ◎ | ◎ | ◎ | ◎ |
| Uniformity of a Film Surface | ◎ | ◎ | Δ | Δ | Δ |
| Adhesion | ◎ | ◎ | ○ | ○ | ○ |

It is recognized that from Table 16 that when sucrose ester resins (Resin(1), (2) in Table 16) were used as a film material good properties were obtained.

On the other hand, when alkyd resin or acrylic resin (Resin (3), (4), (5) in Table 16) were used as a film material, though the drying speed were rapid, the film surface was a little whitened and uniformity of the film appearance were a little inferior to that of the case where sucrose ester resins were used.

From the above results it is recognized that a combination of a specified resin (sucrose ester resin) and a specified solvent composition (the compounds (I) and the compounds (a)) is needed to obtain excellent film properties.

Next, the case where a solvent consisting of the compounds (I) and the compounds (II) was mixed with the other solvent ingredients was examined. The results are shown in Table 17, Table 18 and Table 19.

TABLE 17

| Ingredients | Sample 80 | 81 | 82 | 83 | 84 |
|---|---|---|---|---|---|
| Nitrocellulose | 20.0 | 20.0 | 20.0 | 20.0 | 20.0 |
| Sucrose ester resin | 8.0 | 8.0 | 8.0 | 8.0 | 8.0 |
| Citrate | 8.0 | 8.0 | 8.0 | 8.0 | 8.0 |
| Diethylene glycol diethyl ether (DEGDEE) | 30.0 | 20.0 | 15.0 | 10.0 | — |
| Acetone | 30.0 | 20.0 | 15.0 | 10.0 | — |
| Butyl acetate | — | 20.0 | 30.0 | 40.0 | 60.0 |
| Cororants | 4.0 | 4.0 | 4.0 | 4.0 | 4.0 |
| DEGDEE + Acetone/Total solvent | 100 percent | 66.7 | 50 | 33.3 | 0 |
| The Drying Time | ○ | ○ | ○ | △ | × |
| Ease of Application | ◉ | ◉ | ◉ | ◉ | ◉ |
| Uniformity of a Film Surface | ◉ | ◉ | ◉ | × | — |

In Table 17 butyl acetate, which is a generally used solvent for a manicure, was mixed with a solvent consisting of diethylene glycol diethyl ether, which is one of the compounds (I) and acetone, which is one of the compounds (II). From Table 17 it is recognized that sufficient film properties were maintained when the amount of butyl acetate was less than 50 weight percent per solvent. On the other hand, when the amount of butyl acetate exceeded 50 weight percent per solvent the film properties became worse.

TABLE 18

| Ingredients | Sample 85 | 86 | 87 | 88 | 89 |
|---|---|---|---|---|---|
| Nitrocellulose | 20.0 | 20.0 | 20.0 | 20.0 | 20.0 |
| Sucrose ester resin | 8.0 | 8.0 | 8.0 | 8.0 | 8.0 |
| Citrate | 8.0 | 8.0 | 8.0 | 8.0 | 8.0 |
| Diethylene glycol diethyl ether (DEGDEE) | 30.0 | 20.0 | 15.0 | 10.0 | — |
| Acetone | 30.0 | 20.0 | 15.0 | 10.0 | — |
| Ethylene glycol monoethyl ether | — | 20.0 | 30.0 | 40.0 | 60.0 |
| Cororants | 4.0 | 4.0 | 4.0 | 4.0 | 4.0 |
| DEGDEE + Acetone/Total solvent | 100 percent | 66.7 | 50 | 33.3 | 0 |
| The Drying Time | ○ | ○ | ○ | ○ | ○ |
| Ease of Application | ◉ | ◉ | ◉ | ◉ | ◉ |
| Uniformity of a Film Surface | ◉ | ◉ | ◉ | ◉ | × |

TABLE 19

| Ingredients | Sample 90 | 91 | 92 | 93 | 94 |
|---|---|---|---|---|---|
| Nitrocellulose | 20.0 | 20.0 | 20.0 | 20.0 | 20.0 |
| Sucrose ester resin | 8.0 | 8.0 | 8.0 | 8.0 | 8.0 |
| Citrate | 8.0 | 8.0 | 8.0 | 8.0 | 8.0 |
| Diethylene glycol diethyl ether (DEGDEE) | 30.0 | 20.0 | 15.0 | 10.0 | — |
| Acetone | 30.0 | 20.0 | 15.0 | 10.0 | — |
| Ethylene glycol monobutyl ether | — | 20.0 | 30.0 | 40.0 | 60.0 |
| Cororants | 4.0 | 4.0 | 4.0 | 4.0 | 4.0 |
| DEGDEE + Acetone/Total solvent | 100 percent | 66.7 | 50 | 33.3 | 0 |
| The Drying Time | ○ | ○ | ○ | ○ | ○ |
| Ease of Application | ◉ | ◉ | ◉ | ◉ | ◉ |
| Uniformity of a Film Surface | ◉ | ◉ | ◉ | ◉ | ○ |

In Table 18 and Table 19 alkylene glycol monoethers such as ethylene glycol monoethyl ether or ethylene glycol monobutyl ether were mixed with a solvent consisting of diethylene glycol diethyl ether, which is one of the compounds (I) and acetone, which is one of the compounds (II). From Table 18 and Table 19 it is recognized that sufficient film properties were maintained even when the amount of alkylene glycol monoether was twice of the total amount of diethylene glycol diethyl ether and acetone, and that was different from the results of the above-described case where butyl acetate was used.

Next, a mixed solvent consisting of the compounds (I), (II) and (III) was mixed with a generally used solvent for a manicure, and film properties were examined. The results are shown in Table 20.

TABLE 20

| Ingredients | Sample 95 | 96 | 97 | 98 | 99 |
|---|---|---|---|---|---|
| Nitrocellulose | 20.0 | 20.0 | 20.0 | 20.0 | 20.0 |
| Sucrose ester resin | 8.0 | 8.0 | 8.0 | 8.0 | 8.0 |
| Citrate | 8.0 | 8.0 | 8.0 | 8.0 | 8.0 |
| Diethylene glycol diethyl ether (DEGDEE) | 20.0 | 15.0 | 10.0 | 8.0 | — |
| Acetone | 20.0 | 15.0 | 10.0 | 8.0 | — |
| Ethylene glycol monobutyl ether (EGMBE) | 20.0 | 10.0 | 10.0 | 4.0 | — |
| Butyl acetate | — | 20.0 | 30.0 | 40.0 | 60.0 |
| Cororants | 4.0 | 4.0 | 4.0 | 4.0 | 4.0 |
| DEGDEE + Acetone/Total solvent | 100 percent | 66.7 | 50 | 33.3 | 0 |
| The Drying Time | ○ | ○ | ○ | △ | × |
| Ease of Application | ◉ | ◉ | ◉ | ◉ | ◉ |
| Uniformity of a Film Surface | ◉ | ◉ | ◉ | × | — |

In Table 20 butyl acetate, which is a generally used solvent for a manicure, was mixed with a solvent consisting of diethylene glycol diethyl ether which is one of the compounds (I), acetone which is one of the compounds (II) and ethylene glycol monobutyl ether which is one of the compounds (III). From Table 20 it is recognized that sufficient film properties were maintained when the amount of butyl acetate was less than 50 weight percent per solvent. On the other band, when the amount of butyl acetate exceed 50 weight percent per solvent the film properties became worse.

Next, the combination amounts of the compounds (I) and the compounds (I) were varied and the relations between the combination amounts and the properties of the drying speed, ease of application and uniformity of the film surface were examined. The results are shown in Table 21.

TABLE 21

| Ingredients | Sample 100 | 101 | 102 | 103 | 104 | 105 |
|---|---|---|---|---|---|---|
| Nitrocellulose | 20.0 | 20.0 | 20.0 | 20.0 | 20.0 | 20.0 |
| Sucrose ester resin | 8.0 | 8.0 | 8.0 | 8.0 | 8.0 | 8.0 |
| Citrate | 8.0 | 8.0 | 8.0 | 8.0 | 8.0 | 8.0 |
| Diethylene glycol diethyl ether | — | 1.0 | 15.0 | 45.0 | 59.0 | 60.0 |
| Acetone | 60.0 | 59.0 | 45.0 | 15.0 | 1.0 | — |
| Cororants | 4.0 | 4.0 | 4.0 | 4.0 | 4.0 | 4.0 |
| The Drying Time | ○ | ○ | ○ | ○ | ○ | ○ |
| Ease of Application | △ | ○ | ◉ | ◉ | ◉ | ◉ |
| Uniformity of a Film Surface | ○ | ○ | ◉ | ◉ | ◉ | ○ |

It is recognized from Table 21 that when a combination amount of diethylene glycol diethyl ether, which is one of the compound (I), is 1 to 60 weight percent per the total amount of a sample and a combination amount acetone, which is one of the compound (II), is 1 to 60 weight percent per the total amount of a sample good properties were obtained.

On the other hand, when a combination amount of diethylene glycol diethyl ether and acetone is outside the above-mentioned range, deterioration of some properties were recognized.

Next, the combination amounts of the compounds (I) and the compounds (II) were varied and the relations between the combination amounts and the adhesion were examined. The results are shown in Table 22.

TABLE 22

| Ingredients | Sample | | | | | |
|---|---|---|---|---|---|---|
| | 106 | 107 | 108 | 109 | 110 | 111 |
| Nitrocellulose | 15.0 | 15.0 | 15.0 | 15.0 | 15.0 | 15.0 |
| Sucrose ester resin | 8.0 | 8.0 | 8.0 | 8.0 | 8.0 | 8.0 |
| Citrate | 8.0 | 8.0 | 8.0 | 8.0 | 8.0 | 8.0 |
| Diethylene glycol diethyl ether | 3.0 | 5.0 | 15.0 | 25.0 | 40.0 | 43.0 |
| Acetone | 62.0 | 60.0 | 45.0 | 35.0 | 20.0 | 17.0 |
| Butyl acetate | — | — | 5.0 | 5.0 | 5.0 | 5.0 |
| Cororants | 4.0 | 4.0 | 4.0 | 4.0 | 4.0 | 4.0 |
| Adhesion | ○ | ◎ | ◎ | ◎ | ◎ | ○ |
| The Drying Time | ○ | ○ | ○ | ○ | ○ | ○ |
| Ease of Application | ◎ | ◎ | ◎ | ◎ | ◎ | ◎ |
| Uniformity of a Film Surface | ◎ | ◎ | ◎ | ◎ | ◎ | ◎ |

It is recognized from Table 22 that when a combination amount of diethylene glycol diethyl ether, which is one of the compounds (I), is 5 to 40 weight percent per the total amount of a sample and a combination amount acetone, which is one of the compounds (II), is 20 to 60 weight percent per the total amount of a sample the good adhesion was obtained.

On the other hand, when a combination amount of these ingredients was outside the above-mentioned range, the adhesion was inferior to the adhesion obtained by the above-mentioned condition.

In the following sulfonamide resin was selected and samples containing sulfonamide resin were examined.

Film properties of each samples with different solvent were examined. The results are shown in Table 23.

TABLE 23

| Ingredients | Sample | | |
|---|---|---|---|
| | 112 | 113 | 114 |
| Nitrocellulose | 15.0 | 15.0 | 15.0 |
| Sulfonamide resin | 7.0 | 7.0 | 7.0 |
| Citrate | 4.0 | 4.0 | 4.0 |
| Diethylene glycol diethyl ether | 35.0 | — | — |
| Acetone | 35.0 | — | — |
| Ethylene glycol monoethyl ether | — | 70.0 | — |
| Butyl acetate | — | — | 70.0 |
| Cororants | 4.0 | 4.0 | 4.0 |
| The Drying Time | ○ | ○ | X |
| Ease of Application | ◎ | ◎ | ◎ |
| Uniformity of a Film Surface | ◎ | X | — |

It is recognized from Table 23 that when a mixture of diethylene glycol diethyl ether, which is one of the compounds (I), and acetone, which is one of the compounds (II) was used as a solvent the drying speed in water was rapid and fine film surface with no whitening was obtained.

On the other hand, when butyl acetate, which has been commonly used as a solvent of a manicure, was used as a solvent the film was not dried by dipping in water. When ethylene glycol monoethylether was used as well as the prior art, though film drying was performed, the film surface was whitened and an appearance of the film lacked uniformity.

Further film properties of samples containing a solvent consisting of the compounds (I) and the compounds (II) were examined. The results are shown in Table 24.

TABLE 24

| Ingredients | Sample | | | | |
|---|---|---|---|---|---|
| | 115 | 116 | 117 | 118 | 119 |
| Nitrocellulose | 15.0 | 15.0 | 15.0 | 15.0 | 15.0 |
| Sulfonamide resin | 7.0 | 7.0 | 7.0 | 7.0 | 7.0 |
| Citrate | 4.0 | 4.0 | 4.0 | 4.0 | 4.0 |
| Diethylene glycol diethyl ether | 35.0 | — | — | 35.0 | 17.5 |
| Diethylene glycol dibutyl ether | — | 35.0 | — | — | — |
| Triethylene glycol dimethyl ether | — | — | 35.0 | — | — |
| Acetone | 35.0 | 35.0 | 35.0 | — | 17.5 |
| Methyl ethyl ketone | — | — | — | 35.0 | 35.0 |
| Cororants | 4.0 | 4.0 | 4.0 | 4.0 | 4.0 |
| The Drying Time | ○ | ○ | ○ | ○ | ○ |
| Ease of Application | ◎ | ◎ | ◎ | ◎ | ◎ |
| Uniformity of a Film Surface | ◎ | ◎ | ◎ | ◎ | ◎ |

It is recognized from Table 24 that, when a mixture of the compounds (I) and the compounds (II) was used as a solvent, the drying speed in water was rapid and fine film surface was also obtained.

Next, the samples which use resins of the following (1) to (5) as one of the film materials were evaluated. Further, adhesion to a nail was also evaluated according to the above-described procedure. The results are shown in Table 25.

Resin (1) Toluenesulfonamide/epoxy resin (Sulfonamide resin)
Resin (2) Toluenesulfonamide/formaldehyde resin (Sulfonamide resin)
Resin (3) Phthalic acid/Glycerin/Glycidyl Versatate (Alkyd resin)
Resin (4) Alkyl Acrylate/Alkyl Methacrylate Copolymer (Acrylic resin)
Resin (5) Methacrylic acid/Acrylic acid/2-Hydroxyethyl Methacrylate Copolymer (Acrylic resin)

TABLE 25

| Ingredients | Sample | | | | |
|---|---|---|---|---|---|
| | 120 | 121 | 122 | 123 | 124 |
| Nitrocellulose | 15.0 | 15.0 | 15.0 | 15.0 | 15.0 |
| Resin (1) | 7.0 | | | | |
| Resin (2) | | 7.0 | | | |
| Resin (3) | | | 7.0 | | |
| Resin (4) | | | | 7.0 | |
| Resin (5) | | | | | 7.0 |
| Citrate | 4.0 | 4.0 | 4.0 | 4.0 | 4.0 |
| Diethylene glycol diethyl ether | 35.0 | 35.0 | 35.0 | 35.0 | 35.0 |
| Acetone | 35.0 | 35.0 | 35.0 | 35.0 | 35.0 |
| Cororants | 4.0 | 4.0 | 4.0 | 4.0 | 4.0 |
| The Drying Time | ○ | ○ | ○ | ○ | ○ |
| Ease of Application | ◎ | ◎ | ◎ | ◎ | ◎ |
| Uniformity of a Film Surface | ◎ | ◎ | Δ | Δ | Δ |
| Adhesion | ◎ | ◎ | ○ | ○ | ○ |

It is recognized that from Table 25 that when sulfonamide resins (Resin (1), (2) in Table 25) were used as a film material good properties were obtained.

On the other hand, when alkyd resin or acrylic resin (Resin (3), (4), (5) in Table 25) were used, though the drying speed were rapid, the film surface was a little whitened and uniformity of the film appearance were a little inferior to that of the case where sulfonamide resins were used.

From the above results it is recognized that a combination of a specified resin (sulfonamide resin) and a specified solvent composition (the compounds (I) and the compounds (II)) is needed to obtain excellent film properties.

Next, the case where a solvent consisting of the compounds (I and the compounds (II) was mixed with the other solvent ingredients was examined. The results are shown in Table 26, Table 27 and Table 28.

TABLE 26

| | SAMPLE | | | | |
|---|---|---|---|---|---|
| Ingredients | 125 | 126 | 127 | 128 | 129 |
| Nitrocellulose | 15.0 | 15.0 | 15.0 | 15.0 | 15.0 |
| Sulfonamide resin | 7.0 | 7.0 | 7.0 | 7.0 | 7.0 |
| Citrate | 4.0 | 4.0 | 4.0 | 4.0 | 4.0 |
| Diethylene glycol diethyl ether (DEGDEE) | 35.0 | 23.3 | 17.5 | 11.7 | — |
| Acetone | 35.0 | 23.3 | 17.5 | 11.7 | — |
| Butyl acetate | — | 23.3 | 35.0 | 46.6 | 70.0 |
| Cororants | 4.0 | 4.0 | 4.0 | 4.0 | 4.0 |
| DEGDEE + Acetone/ Total solvent | 100 percent | 66.7 | 50 | 33.3 | 0 |
| The Drying Time | ○ | ○ | ○ | Δ | × |
| Ease of Application | ⊚ | ⊚ | ⊚ | ⊚ | ⊚ |
| Uniformity of a Film Surface | ⊚ | ⊚ | ⊚ | × | — |

In Table 26 butyl acetate, which is a generally used solvent for a manicure, was mixed with a solvent consisting of diethylene glycol diethyl ether, which is one of the compounds (I) and acetone, which is one of the compounds (II). From Table 26 it is recognized that sufficient film properties were maintained when the amount of butyl acetate was less than 50 weight percent per solvent. On the other hand, when the amount of butyl acetate exceeded 50 weight percent per solvent the film properties became worse.

TABLE 27

| | SAMPLE | | | | |
|---|---|---|---|---|---|
| Ingredients | 130 | 131 | 132 | 133 | 134 |
| Nitrocellulose | 15.0 | 15.0 | 15.0 | 15.0 | 15.0 |
| Sulfonamide resin | 7.0 | 7.0 | 7.0 | 7.0 | 7.0 |
| Citrate | 4.0 | 4.0 | 4.0 | 4.0 | 4.0 |
| Diethylene glycol diethyl ether (DEGDEE) | 35.0 | 23.3 | 17.5 | 11.7 | — |
| Acetone | 35.5 | 23.3 | 17.5 | 11.7 | — |
| Ethylene glycol monoethyl ether | — | 23.3 | 35.0 | 46.6 | 70.0 |
| Cororants | 4.0 | 4.0 | 4.0 | 4.0 | 4.0 |
| DEGDEE + Acetone/ Total solvent | 100 percent | 66.7 | 50 | 33.3 | 0 |
| The Drying Time | ○ | ○ | ○ | ○ | ○ |
| Ease of Application | ⊚ | ⊚ | ⊚ | ⊚ | ⊚ |
| Uniformity of a Film Surface | ⊚ | ⊚ | ⊚ | ⊚ | × |

TABLE 28

| | SAMPLE | | | | |
|---|---|---|---|---|---|
| Ingredients | 135 | 136 | 137 | 138 | 139 |
| Nitrocellulose | 15.0 | 15.0 | 15.0 | 15.0 | 15.0 |
| Sulfonamide resin | 7.0 | 7.0 | 7.0 | 7.0 | 7.0 |
| Citrate | 4.0 | 4.0 | 4.0 | 4.0 | 4.0 |
| Diethylene glycol diethyl ether (DEGDEE) | 35.0 | 23.3 | 17.5 | 11.7 | — |
| Acetone | 35.0 | 23.3 | 17.5 | 11.7 | — |
| Ethylene glycol monobutyl ether | — | 23.3 | 35.0 | 46.6 | 70.0 |

TABLE 28-continued

| | SAMPLE | | | | |
|---|---|---|---|---|---|
| Ingredients | 135 | 136 | 137 | 138 | 139 |
| Cororants | 4.0 | 4.0 | 4.0 | 4.0 | 4.0 |
| DEGDEE + Acetone/ Total solvent | 100 percent | 66.7 | 50 | 33.3 | 0 |
| The Drying Time | ○ | ○ | ○ | ○ | ○ |
| Ease of Application | ⊚ | ⊚ | ⊚ | ⊚ | ⊚ |
| Uniformity of a Film Surface | ⊚ | ⊚ | ⊚ | ⊚ | ○ |

In Table 27 and Table 28 alkylene glycol monoethers such as ethylene glycol monoethyl ether or ethylene glycol monobutyl ether were mixed with a solvent consisting of diethylene glycol diethyl ether, which is one of the compounds (I) and acetone, which is one of the compounds (II). From Table 27 and Table 28 it is recognized that sufficient film properties were maintained even when the amount of alkylene glycol monoether was twice of the total amount of diethylene glycol diethyl ether and acetone, and that was different from the results of the above-described case where butyl acetate was used.

Next, a mixed solvent consisting of the compounds (I), (II) and (III) was mixed with a generally used solvent for a manicure, and film properties were examined. The results are shown in Table 29.

TABLE 29

| | SAMPLE | | | | |
|---|---|---|---|---|---|
| Ingredients | 140 | 141 | 142 | 143 | 144 |
| Nitrocellulose | 15.0 | 15.0 | 15.0 | 15.0 | 15.0 |
| Sulfonamide resin | 7.0 | 7.0 | 7.0 | 7.0 | 7.0 |
| Citrate | 4.0 | 4.0 | 4.0 | 4.0 | 4.0 |
| Diethylene glycol diethyl ether (DEGDEE) | 23.3 | 20.0 | 15.0 | 10.0 | — |
| Acetone | 23.3 | 20.0 | 15.0 | 10.0 | — |
| Ethylene glycol monobutyl ether (EGMBE) | 23.3 | 6.7 | 5.0 | 3.4 | — |
| Butyl acetate | — | 23.3 | 35.0 | 46.6 | 70.0 |
| Cororants | 4.0 | 4.0 | 4.0 | 4.0 | 4.0 |
| DEGDEE + Acetone/ Total solvent | 100 percent | 66.7 | 50 | 33.3 | 0 |
| The Drying Time | ○ | ○ | ○ | ○ | ○ |
| Ease of Application | ⊚ | ⊚ | ⊚ | ⊚ | ⊚ |
| Uniformity of a Film Surface | ⊚ | ⊚ | ⊚ | ⊚ | ○ |

In Table 29 butyl acetate, which is a generally used solvent for a manicure, was mixed with a solvent consisting of diethylene glycol diethyl ether which is one of the compounds (I), acetone which is one of the compounds (II) and ethylene glycol monobutyl ether which is one of the compounds (III). From Table 29 it is recognized that sufficient film properties were maintained when the amount of butyl acetate was less than 50 weight percent per solvent On the other hand, when the amount of butyl acetate exceeded 50 weight percent per solvent the film properties became worse.

Next, the combination amounts of the compounds (I) and the compounds (II) were varied and the relations between the combination amounts and the properties of the drying speed, ease of application and uniformity of the film surface were examined. The results are shown in Table 30.

TABLE 30

| Ingredients | Sample | | | | | |
|---|---|---|---|---|---|---|
| | 145 | 146 | 147 | 148 | 149 | 150 |
| Nitrocellulose | 15.0 | 15.0 | 15.0 | 15.0 | 15.0 | 15.0 |
| Sulfonamide resin | 7.0 | 7.0 | 7.0 | 7.0 | 7.0 | 7.0 |
| Citrate | 4.0 | 4.0 | 4.0 | 4.0 | 4.0 | 4.0 |
| Diethylene glycol diethyl ether | — | 1.0 | 20.0 | 46.0 | 65.0 | 66.0 |
| Acetone | 66.0 | 65.0 | 46.0 | 20.0 | 1.0 | — |
| Butyl acetate | 4.0 | 4.0 | 4.0 | 4.0 | 4.0 | 4.0 |
| Cororants | 4.0 | 4.0 | 4.0 | 4.0 | 4.0 | 4.0 |
| The Drying Time | ○ | ○ | ○ | ○ | ○ | ○ |
| Ease of Application | △ | ○ | ◎ | ◎ | ◎ | ◎ |
| Uniformity of a Film Surface | ○ | ○ | ◎ | ◎ | ◎ | ○ |

It is recognized from Table 30 that when a combination amount of diethylene glycol diethyl ether, which is one of the compound (I), is 1 to 65 weight percent per the total amount of a sample and a combination amount acetone, which is one of the compound (II), is 1 to 65 weight percent per the total amount of a sample good properties were obtained.

On the other hand, when a combination amount of diethylene glycol diethyl ether and acetone is outside the above-mentioned range, deterioration of some properties were recognized.

Next, the combination amounts of the compounds (I) and the compounds (II) were varied and the relations between the combination amounts and the adhesion were examined. The results are shown in Table 31.

TABLE 31

| Ingredients | Sample | | | | | |
|---|---|---|---|---|---|---|
| | 151 | 152 | 153 | 154 | 155 | 156 |
| Nitrocellulose | 15.0 | 15.0 | 15.0 | 15.0 | 15.0 | 15.0 |
| Sulfonamide resin | 7.0 | 7.0 | 7.0 | 7.0 | 7.0 | 7.0 |
| Citrate | 4.0 | 4.0 | 4.0 | 4.0 | 4.0 | 4.0 |
| Diethylene glycol diethyl ether | 7.0 | 10.0 | 25.0 | 40.0 | 50.0 | 53.0 |
| Acetone | 63.0 | 60.0 | 45.0 | 25.0 | 15.0 | 12.0 |
| Butyl acetate | — | — | — | 5.0 | 5.0 | 5.0 |
| Cororants | 4.0 | 4.0 | 4.0 | 4.0 | 4.0 | 4.0 |
| Adhesion | ○ | ◎ | ◎ | ◎ | ◎ | ○ |
| The Drying Time | ○ | ○ | ○ | ○ | ○ | ○ |
| Ease of Application | ◎ | ◎ | ◎ | ◎ | ◎ | ◎ |
| Uniformity of a Film Surface | ◎ | ◎ | ◎ | ◎ | ◎ | ◎ |

It is recognized from Table 31 that when a combination amount of diethylene glycol diethyl ether, which is one of the compound (I), is 10 to 50 weight percent per the total amount of a sample and a combination amount acetone, which is one of the compound (II), is 15 to 60 weight percent per the total amount of a sample the adhesion was very good.

On the other hand, when a combination amount of these ingredients was outside the above-mentioned range, the adhesion was inferior to the very good adhesion obtained by the above-mentioned condition.

Further, the drying time, ease of application and uniformity of film surface were evaluated for samples which use sucrose ester or sulfonamide as a resin and having variable solvent compositions. The results are shown in Table 32 to Table 37.

TABLE 32

| Ingredients | Sample | | | | | |
|---|---|---|---|---|---|---|
| | 157 | 158 | 159 | 160 | 161 | 162 |
| Nitrocellulose | 20 | 20 | 20 | 20 | 20 | 20 |
| Sucrose ester resin | 8 | 8 | 8 | 8 | 8 | 8 |
| Citrate | 8 | 8 | 8 | 8 | 8 | 8 |
| DEGDEE | 10 | 30 | 15 | 20 | 10 | 15 |
| MEK | 45 | — | — | 20 | 15 | 30 |
| Acetone | 5 | 30 | 45 | 20 | 35 | 15 |
| Cororants | 4 | 4 | 4 | 4 | 4 | 4 |
| The Drying Time | ○ | ○ | ○ | ○ | ○ | ○ |
| Ease of Application | ◎ | ◎ | ◎ | ◎ | ◎ | ◎ |
| Uniformity of a Film Surface | ◎ | ◎ | ◎ | ◎ | ◎ | ◎ |

DEGDEE: Diethylene glycol diethyl ether
MEK: Methyl ethyl ketone

TABLE 33

| Ingredients | Sample | |
|---|---|---|
| | 163 | 164 |
| Nitrocellulose | 20 | 20 |
| Sucrose ester resin | 8 | 8 |
| Citrate | 8 | 8 |
| DEGDEE | 10 | 10 |
| MEK | 30 | 40 |
| Acetone | 20 | 10 |
| Cororants | 4 | 4 |
| The Drying Time | ○ | ○ |
| Ease of Application | ◎ | ◎ |
| Uniformity of a Film Surface | ◎ | ◎ |

TABLE 34

| Ingredients | Sample | | | | | |
|---|---|---|---|---|---|---|
| | 165 | 166 | 167 | 168 | 169 | 170 |
| Nitrocellulose | 20 | 20 | 20 | 20 | 20 | 20 |
| Sucrose ester resin | 8 | 8 | 8 | 8 | 8 | 8 |
| Citrate | 8 | 8 | 8 | 8 | 8 | 8 |
| DEGDEE | 10 | 30 | 15 | 20 | 10 | 15 |
| EGDEE | 45 | — | — | 20 | 15 | 30 |
| Acetone | 5 | 30 | 45 | 20 | 35 | 15 |
| Cororants | 4 | 4 | 4 | 4 | 4 | 4 |
| The Drying Time | ○ | ○ | ○ | ○ | ○ | ○ |
| Ease of Application | ◎ | ◎ | ◎ | ◎ | ◎ | ◎ |
| Uniformity of a Film Surface | ◎ | ◎ | ◎ | ◎ | ◎ | ◎ |

EGDEE: Ethylene glycol diethyl ether

TABLE 35

| Ingredients | Sample | | | |
|---|---|---|---|---|
| | 171 | 172 | 173 | 174 |
| Nitrocellulose | 20 | 20 | 20 | 20 |
| Sucrose ester resin | 8 | 8 | 8 | 8 |
| Citrate | 8 | 8 | 8 | 8 |
| DEGDEE | 10 | 10 | 45 | 35 |
| EGDEE | 30 | 40 | — | 15 |
| Acetone | 20 | 10 | 15 | 10 |
| Cororants | 4 | 4 | 4 | 4 |
| The Drying Time | ○ | ○ | ○ | ○ |
| Ease of Application | ◎ | ◎ | ◎ | ◎ |
| Uniformity of a Film Surface | ◎ | ◎ | ◎ | ◎ |

TABLE 36

| Ingredients | Sample | | | | | | |
|---|---|---|---|---|---|---|---|
| | 175 | 176 | 177 | 178 | 179 | 180 | 181 |
| Nitrocellulose | 15.0 | 15.0 | 15.0 | 15.0 | 15.0 | 15.0 | 15.0 |
| Sulfonamide resin | 7.0 | 7.0 | 7.0 | 7.0 | 7.0 | 7.0 | 7.0 |
| Citrate | 4.0 | 4.0 | 4.0 | 4.0 | 4.0 | 4.0 | 4.0 |
| DEGDEE | 35.0 | 20.0 | 12.5 | 17.5 | 50.0 | 10.0 | 27.0 |
| MEK | — | — | 17.5 | 35.0 | 10.0 | 35.0 | 16.0 |
| Acetone | 35.0 | 50.0 | 40.0 | 17.5 | 10.0 | 25.0 | 27.0 |
| Cororants | 4.0 | 4.0 | 4.0 | 4.0 | 4.0 | 4.0 | 4.0 |
| The Drying Time | ○ | ○ | ○ | ○ | ○ | ○ | ○ |
| Ease of Application | ◎ | ◎ | ◎ | ◎ | ◎ | ◎ | ◎ |
| Uniformity of a Film Surface | ◎ | ◎ | ◎ | ◎ | ◎ | ◎ | ◎ |

TABLE 37

| Ingredients | Sample | | | | | | |
|---|---|---|---|---|---|---|---|
| | 182 | 183 | 184 | 185 | 186 | 187 | 188 |
| Nitrocellulose | 15.0 | 15.0 | 15.0 | 15.0 | 15.0 | 15.0 | 15.0 |
| Sulfonamide resin | 7.0 | 7.0 | 7.0 | 7.0 | 7.0 | 7.0 | 7.0 |
| Citrate | 4.0 | 4.0 | 4.0 | 4.0 | 4.0 | 4.0 | 4.0 |
| DEGDEE | 35.0 | 20.0 | 12.5 | 17.5 | 50.0 | 10.0 | 27.0 |
| EGDEE | — | — | 17.5 | 35.0 | 10.0 | 35.0 | 16.0 |
| Acetone | 35.0 | 50.0 | 40.0 | 17.5 | 10.0 | 25.0 | 27.0 |
| Cororants | 4.0 | 4.0 | 4.0 | 4.0 | 4.0 | 4.0 | 4.0 |
| The Drying Time | ○ | ○ | ○ | ○ | ○ | ○ | ○ |
| Ease of Application | ◎ | ◎ | ◎ | ◎ | ◎ | ◎ | ◎ |
| Uniformity of a Film Surface | ◎ | ◎ | ◎ | ◎ | ◎ | ◎ | ◎ |

These samples showed sufficient properties of the drying time, ease of application and uniformity of a film surface.

EXAMPLES

Concrete examples of the present invention are shown in the following. Examples of the case where the composition of the present invention is used for manicure are shown.

Example 1

| Nitrocellulose | 20.0 weight percent |
|---|---|
| Sucrose ester resin | 8.0 |
| Citrate | 8.0 |
| Diethylene glycol diethyl ether | 20.0 |
| Acetone | 20.0 |
| Methyl ethyl ketone | 20.0 |
| Cororants | 4.0 |

Example 2

| Nitrocellulose | 20.0 |
|---|---|
| Sucrose ester resin | 8.0 |
| Citrate | 8.0 |
| Diethylene glycol diethyl ether | 30.0 |
| Acetone | 30.0 |
| Cororants | 4.0 |

Example 3

| Nitrocellulose | 15.0 |
|---|---|
| Suifonamide resin | 7.0 |
| Citrate | 4.0 |
| Diethylene glycol diethyl ether | 35.0 |
| Acetone | 35.0 |
| Cororants | 4.0 |

Example 4

| Nitrocellulose | 15.0 |
|---|---|
| Suifonamide resin | 7.0 |
| Citrate | 4.0 |
| Diethylene glycol diethyl ether | 27.0 |
| Acetone | 27.0 |
| Methyl ethyl ketone | 16.0 |
| Cororants | 4.0 |

Example 5

| Nitrocellulose | 15.0 |
|---|---|
| Suifonamide resin | 7.0 |
| Citrate | 4.0 |
| Triethylene glycol dimethyl ether | 12.5 |
| Ethylene glycol diethyl ether | 17.5 |
| Acetone | 37.5 |
| Cororants | 4.0 |
| Viscosity controlling agent | 1.5 |
| Ultraviolet absorber | 1.0 |

Example 6

| Nitrocellulose | 20.0 |
|---|---|
| Sucrose ester resin | 8.0 |
| Citrate | 8.0 |
| Ethylene glycol diethyl ether | 15.0 |
| Diethylene glycol diethyl ether | 35.0 |
| Acetone | 10.0 |
| Cororants | 4.0 |

Example 7

| Nitrocellulose | 20.0 |
|---|---|
| Sucrose ester resin | 8.0 |
| Citrate | 8.0 |
| Ethylene glycol diethyl ether | 30.0 |
| Diethylene glycol diethyl ether | 10.0 |
| Acetone | 20.0 |
| Cororants | 4.0 |

Example 8

| Nitrocellulose | 15.0 |
|---|---|
| Suifonamide resin | 7.0 |
| Citrate | 4.0 |
| Triethylene glycol dimethyl ether | 35.0 |
| Acetone | 35.0 |
| Cororants | 4.0 |

Example 9

| Nitrocellulose | 15.0 |
|---|---|
| Suifonamide resin | 7.0 |
| Citrate | 4.0 |
| Diethylene glycol diethyl ether | 47.5 |
| Acetone | 10.0 |
| Methyl ethyl ketone | 10.0 |
| Cororants | 4.0 |
| Viscosity controlling agent | 1.5 |
| Ultraviolet absorber | 1.0 |

Example 10

| Nitrocellulose | 20.0 |
|---|---|
| Sucrose ester resin | 8.0 |
| Citrate | 8.0 |
| Diethylene glycol diethyl ether | 10.0 |
| Acetone | 5.0 |
| Methyl ethyl ketone | 45.0 |
| Cororants | 4.0 |

Example 11

| Nitrocellulose | 20.0 |
|---|---|
| Sucrose ester resin | 8.0 |
| Citrate | 8.0 |
| Diethylene glycol diethyl ether | 15.0 |
| Acetone | 45.0 |
| Cororants | 4.0 |

Example 12

| Nitrocellulose | 20.0 |
|---|---|
| Sucrose ester resin | 8.0 |
| Citrate | 8.0 |
| Diethylene glycol diethyl ether | 10.0 |
| Acetone | 35.0 |
| Methyl ethyl ketone | 15.0 |
| Cororants | 4.0 |

-continued

| Example 13 | |
|---|---|
| Nitrocellulose | 20.0 |
| Sucrose ester resin | 8.0 |
| Citrate | 8.0 |
| Diethylene glycol diethyl ether | 15.0 |
| Acetone | 15.0 |
| Methyl ethyl ketone | 30.0 |
| Cororants | 4.0 |

| Example 14 | |
|---|---|
| Nitrocellulose | 20.0 |
| Sucrose ester resin | 8.0 |
| Citrate | 8.0 |
| Ethylene glycol diethyl ether | 10.0 |
| Acetone | 5.0 |
| Methyl ethyl ketone | 42.5 |
| Cororants | 4.0 |
| Viscosity controlling agent | 1.5 |
| Ultraviolet absorber | 1.0 |

| Example 15 | |
|---|---|
| Nitrocellulose | 20.0 |
| Sucrose ester resin | 8.0 |
| Citrate | 8.0 |
| Diethylene glycol diethyl ether | 10.0 |
| Acetone | 20.0 |
| Methyl ethyl ketone | 30.0 |
| Cororants | 4.0 |

| Example 16 | |
|---|---|
| Nitrocellulose | 20.0 |
| Sucrose ester resin | 8.0 |
| Citrate | 8.0 |
| Diethylene glycol diethyl ether | 10.0 |
| Acetone | 10.0 |
| Methyl ethyl ketone | 40.0 |
| Cororants | 4.0 |

| Example 17 | |
|---|---|
| Nitrocellulose | 20.0 |
| Sucrose ester resin | 8.0 |
| Citrate | 8.0 |
| Diethylene glycol diethyl ether | 10.0 |
| Acetone | 5.0 |
| Methyl ethyl ketone | 45.0 |
| Cororants | 4.0 |

| Example 18 | |
|---|---|
| Nitrocellulose | 20.0 |
| Sucrose ester resin | 8.0 |
| Citrate | 8.0 |
| Ethylene glycol diethyl ether | 15.0 |
| Diethylene glycol diethyl ether | 10.0 |
| Acetone | 35.0 |
| Cororants | 4.0 |

| Example 19 | |
|---|---|
| Nitrocellulose | 20.0 |
| Sucrose ester resin | 8.0 |
| Citrate | 8.0 |
| Ethylene glycol dibutyl ether | 30.0 |
| Diethylene glycol diethyl ether | 10.0 |
| Acetone | 20.0 |
| Cororants | 4.0 |

| Example 20 | |
|---|---|
| Nitrocellulose | 20.0 |
| Sucrose ester resin | 8.0 |
| Citrate | 8.0 |
| Diethylene glycol diethyl ether | 30.0 |
| Acetone | 27.5 |
| Cororants | 4.0 |
| Viscosity controlling agent | 1.5 |
| Ultraviolet absorber | 1.0 |

| Example 21 | |
|---|---|
| Nitrocellulose | 15.0 |
| Sulfonamide resin | 7.0 |
| Citrate | 4.0 |
| Diethylene glycol diethyl ether | 20.0 |
| Acetone | 50.0 |
| Cororants | 4.0 |

| Example 22 | |
|---|---|
| Nitrocellulose | 15.0 |
| Sulfonamide resin | 7.0 |
| Citrate | 4.0 |
| Diethylene glycol diethyl ether | 12.5 |
| Acetone | 40.0 |
| Methyl ethyl ketone | 17.5 |
| Cororants | 4.0 |

| Example 23 | |
|---|---|
| Nitrocellulose | 15.0 |
| Sulfonamide resin | 7.0 |
| Citrate | 4.0 |
| Diethylene glycol diethyl ether | 17.5 |
| Acetone | 17.5 |
| Methyl ethyl ketone | 35.0 |
| Cororants | 4.0 |

| Example 24 | |
|---|---|
| Nitrocellulose | 15.0 |
| Sulfonamide resin | 7.0 |
| Citrate | 4.0 |
| Ethylene glycol diethyl ether | 27.0 |
| Acetone | 27.0 |
| Methyl ethyl ketone | 16.0 |
| Cororants | 4.0 |

| Example 25 | |
|---|---|
| Nitrocellulose | 15.0 |
| Sulfonamide resin | 7.0 |
| Citrate | 4.0 |
| Diethylene glycol diethyl ether | 12.5 |
| Ethylene glycol diethyl ether | 17.5 |
| Acetone | 37.5 |
| Cororants | 4.0 |
| Viscosity controlling agent | 1.5 |
| Ultraviolet absorber | 1.0 |

These examples showed excellent film drying properties in water and uniformity of the film surface.

As described above, the film composition of the present invention gives good film-forming property in water and uniformity of the film surface by use of specified alkylene glycol ethers and ketones as solvent ingredients. Moreover, further detail selection of resins and solvents gives an excellent composition as manicure.

What is claimed is:

1. A film forming composition which forms a solidified film upon exposure to air within 2 to 10 minutes after application and which forms a solidified film in water when dipped in less than 2 minutes after application, said composition comprising water insoluble film materials, and a solvent which dissolves said water insoluble film materials and is soluble in water, wherein said solvent contains one or more solvent ingredients selected from compounds of the following formula (I), formula (II) and formula (III),:

(I)

wherein $R_1$ and $R_2$ are each a $C_1$ to $C_{18}$ alkyl or acyl groups, $R_3$ and $R_4$ are each H or a $C_1$ to $C_{18}$ alkyl group, and m and n are an integral number of 1 to 20;

wherein $R_5$ and $R_6$ are each a $C_1$ to $C_{18}$ alkyl group; and wherein $R_7$ is a $C_3$ to $C_{18}$ alkyl or acyl group.

2. The film forming composition according to claim 1 wherein the total amount of the compounds (I), (II) and (III) in the composition is more than 50 weight percent of the solvent.

3. The film forming composition according to claim 2 wherein the amount of the compounds (I) is 15 to 60 weight percent of the solvent and the amount of the compounds (II) is 30 to 70 weight percent of the solvent.

4. The film forming composition according to claim 1 wherein the compounds (I) are one or more compounds selected from ethylene glycol dimethyl ether, ethylene glycol diethyl ether, ethylene glycol dipropyl ether, ethylene glycol dibutyl ether, ethylene glycol dipentyl ether, diethylene glycol dimethyl ether, diethylene glycol diethyl ether, diethylene glycol dipropyl ether, diethylene glycol dibutyl ether, triethylene glycol dimethyl ether, triethylene glycol diethyl ether, triethylene glycol dipropyl ether, and triethylene glycol dibutyl ether.

5. The film forming composition according to claim 1 wherein the compounds (II) are one or more compounds selected from acetone, methyl ethyl ketone, 3-methyl-2-butanone, 3-pentanone, 2-pentanone, 2-methyl-3-pentanone, 3-hexanone, 2-hexanone, 3-methyl-2-pentanone and 4-methyl-2-pentanone.

6. The film forming composition according to claim 1 wherein the compounds (III) are one or more compounds selected from ethylene glycol monopropyl ether, ethylene glycol monobutyl ether, ethylene glycol monopentyl ether and ethylene glycol monohexyl ether.

7. The film forming composition according to claim 1 wherein one or more solvent ingredients selected from the compounds of the following formula (IV), alcohols, polyhydric alcohols and the compounds of the following formula (V) are further contained in the solvent of the composition:

wherein $R_8$ is a $C_1$ to $C_{18}$ alkyl or acyl group and $R_9$ and $R_{10}$ are each H or a $C_1$ to $C_{18}$ alkyl group and p and q are an integral number of 1 to 20; and wherein $R_{11}$ and $R_{12}$ are each a $C_1$ to $C_{18}$ alkyl group.

8. The film forming composition according to claim 1 wherein the amount of the compounds (I) is more than 50 weight percent of the solvent.

9. The film forming composition according to claim 8 wherein the solvent further contains one or more ingredients selected from the compounds (II) and the compounds (III).

10. The film forming composition according to claim 1 wherein the solvent contains more than 50 weight percent of acetone, methyl ethyl ketone or their mixture and more than 15 weight percent of solvent ingredients with a boiling point of more than 100° C. which are soluble in acetone, methyl ethyl ketone or mixtures thereof.

11. The film forming composition according to claim 10 wherein the solvent ingredients with a boiling point of more than 100° C. are selected from compounds (I), (II) and (III).

12. A manicuring composition for nails comprising water insoluble film materials and a solvent which dissolves said film materials and is soluble in water, wherein said solvent contains one or more selected from said compounds (I), (II), and (III), and wherein said film materials comprise nitrocellulose, a sucrose ester resin and an organic ester plasticizer and wherein the compound (I) is 1 to 60 weight percent based on the weight of the composition, and the compound (II) is 1 to 60 weight percent based on the weight of the composition.

13. The manicuring composition according to claim 12 wherein total amount of the compounds (I), (II) and (III) is more than 50 weight percent solvent.

14. The manicuring composition according to claim 13 wherein the compound (I) is 5 to 40 weight percent of the composition and the compound (II) is 20 to 60 weight percent of the composition.

15. The manicuring composition according to claim 12 wherein the compounds (I) are one or more compounds selected from ethylene glycol dimethyl ether, ethylene glycol diethyl ether, ethylene glycol dipropyl ether, ethylene glycol dibutyl ether, ethylene glycol dipentyl ether, diethylene glycol dimethyl ether, diethylene glycol diethyl ether, diethylene glycol dipropyl ether, diethylene glycol dibutyl ether, triethylene glycol dimethyl ether, triethylene glycol diethyl ether, triethylene glycol dipropyl ether and triethylene glycol dibutyl ether.

16. Then manicuring composition according to claim 12 wherein the compounds (II) are one or more compounds selected from acetone, methyl ethyl ketone, 3-methyl-2-butanone, 3-pentanone, 2-pentanone, 2-methyl-3-pentanone, 3-hexanone, 2-hexanone, 3-methyl-2-pentanone and 4-methyl-2-pentanone.

17. The manicuring composition according to claim 12 wherein the compounds (III) are one or more compounds selected from ethylene glycol monopropyl ether, ethylene glycol monobutyl ether, ethylene glycol monopentyl ether and ethylene glycol monohexyl ether.

18. The manicuring composition according to claim 12 wherein one or more solvent ingredients selected from said compounds (IV), alcohols, polyhydric alcohols and said compounds (V) are further contained in the solvent:

wherein $R_8$ is a $C_1$ to $C_{18}$ alkyl or acyl group and $R_9$ and $R_{10}$ are each H or a $C_1$ to $C_{18}$ alkyl group and p and g are an integral number of 1 to 20; and wherein $R_{11}$ and $R_{12}$ are each a $C_1$ to $C_{18}$ alkyl group.

19. A manicuring composition for nails comprising water insoluble film materials and a solvent which dissolves said film materials and is soluble in water, wherein said solvent contains one or more selected from said compounds (I), (II), and (III), and wherein, nitrocellulose, sulfonamide resin and organic ester plasticizer are comprised as said film materials, and the compound (I) is 1 to 65 weight percent based upon the weight of the composition and the compound (II) is 1 to 65 weight percent based upon the weight of the composition.

20. The manicuring composition according to claim 19 wherein total amount of the compounds (I), (II) and (III) in the composition is more than 50 weight percent of the solvent.

21. The manicuring composition according to claim 20 wherein the compound (I) is 10 to 50 weight percent based upon the weight of the composition and the compound (II) is 15 to 60 weight percent based on the weight of the composition.

22. The manicuring composition according to claim 19 wherein the compounds (I) are one or more compounds selected from ethylene glycol dimethyl ether, ethylene glycol diethyl ether, ethylene glycol dipropyl ether, ethylene glycol dibutyl ether, ethylene glycol dipentyl ether, diethylene glycol dimethyl ether, diethylene glycol diethyl ether, diethylene glycol dipropyl ether, diethylene glycol dibutyl ether, triethylene glycol dimethyl ether, triethylene glycol diethyl ether, triethylene glycol dipropyl ether and triethylene glycol dibutyl ether.

23. The manicuring composition according to claim 19 wherein the compounds (II) are one or more compounds selected from acetone, methyl ethyl ketone, 3-methyl-2-butanone, 3-pentanone, 2-pentanone, 2-methyl-3-pentanone, 3-hexanone, 2-hexanone, 3-methyl-2-pentanone and 4-methyl-2-pentanone.

24. The manicuring composition according to claim 19 wherein the compounds (III) are one or more compounds selected from ethylene glycol monopropyl ether, ethylene glycol monobutyl ether, ethylene glycol monopentyl ether and ethylene glycol monohexyl ether.

25. The manicuring composition according to claim 19 wherein one or more solvent ingredients selected from said compounds (IV), alcohols, polyhydric alcohols and said compounds (V) are further contained in said solvent;

wherein $R_8$ is a $C_1$ to $C_{18}$ alkyl or acyl group and $R_9$ and $R_{10}$ are each H or a $C_1$ to $C_{18}$ alkyl group and p and g are an integral number of 1 to 20; and wherein $R_{11}$ and $R_{12}$ are each a $C_1$ to $C_{18}$ alkyl group.

26. The manicuring composition according to claim 12 which is a dual manicure composition which forms a solidified film upon exposure to air within 2 to 10 minutes after the manicure is applied on a nail and which forms a solidified film in water when dipped in water in less than 2 minutes after the manicure is applied on a nail.

27. A film forming method comprising the steps of:
applying a film forming composition onto a material to be treated; and
dipping said treated material in water to form a solidified film on the treated material, wherein said film forming composition comprises a water insoluble film material and a solvent which dissolves said water insoluble film materials and is soluble in water, wherein said solvent contains one or more solvent ingredients selected from compounds of the following formula (I), formula (II) and formula (III):

wherein $R_1$ and $R_2$ are each a $C_1$ to $C_{18}$ alkyl or acyl group, $R_3$ and $R_4$ each H or a $C_1$ to $C_{18}$ alkyl group and m and n are an integral number of 1 to 20;

wherein $R_5$ and $R_6$ are each a $C_1$ to $C_{18}$ alkyl group; and wherein $R_7$ is a $C_3$ to $C_{18}$ alkyl or acyl group.

28. The film forming method according to claim 27 wherein the solidified film is formed in water by dipping in water in less than 2 minutes.

29. The film forming method according to claim 27 wherein said formula (I) compounds are one or more compounds selected from ethylene glycol dimethyl ether, ethylene glycol diethyl ether, ethylene glycol dipropyl ether, ethylene glycol dibutyl ether, ethylene glycol dipentyl ether, diethylene glycol dimethyl ether, diethylene glycol diethyl ether, diethylene glycol dipropyl ether, diethylene glycol dibutyl ether, triethylene glycol dimethyl ether, triethylene glycol diethyl ether, triethylene glycol dipropyl ether and triethylene glycol dibutyl ether.

30. The film forming method according to claim 27 wherein said formula (II) compounds are one or more compounds selected from acetone, methyl ethyl ketone, 3-methyl-2-butanone, 3-pentanone, 2-pentanone, 2-methyl-3-pentanone, 3-hexanone, 2-hexanone, 3-methyl-2-pentanone and 4-methyl-2-pentanone.

31. The film forming method according to claim 27 wherein said formula (III) compounds are one or more compounds selected from ethylene glycol monopropyl ether, ethylene glycol monobutyl ether, ethylene glycol monopentyl ether and ethylene glycol monohexyl ether.

32. The film forming composition according to claim 1 wherein $R_1$, $R_2$, $R_3$, and $R_4$ are $C_1$ to $C_{10}$ alkyl groups and p and q are an integral number of 1 to 10.

33. The film forming composition according to claim 1 wherein $R_5$ and $R_6$ are $C_1$ to $C_6$ alkyl groups.

34. The film forming composition according to claim 1 wherein $R_7$ is a $C_1$ to $C_{10}$ alkyl group.

35. The film forming composition according to claim 1 wherein said film materials comprise one or more plasticizers selected from dibutyl phthalate, dioctyl phthalate, tributyl citrate, acetyl tributyl citrate, acetyl triethyl citrate and camphor.

36. The film forming composition according to claim 1 wherein said film materials comprise one or more resins selected from alkyd resin, acrylic resin, acrylic silicone resin, polyester resin, sucrose resin, sulfonamide resin, rosin, phenolic resin, amino resin, and epoxy resin.

37. The film forming composition according to claim 1, wherein said film materials comprise nitrocellulose as a film forming ingredient.

38. A manicuring composition for nails consisting of the film forming composition according to claim 1.

39. The manicuring composition according to claim 19, which is a dual manicure composition which forms a solidified film upon exposure to air within 2 to 10 minutes after the manicure is applied on a nail and which forms a solidified film in water when dipped in water in less than 2 minutes after the manicure is applied on a nail.

40. The film forming method according to claim 27, wherein said solvent is that mentioned in any of claims 2–3, 7–9, and 10–11.

41. The film forming method according to claim 27, wherein said film materials contains a plasticizer mentioned in claim 35, a resin mentioned in claim 36 and nitrocellulose.

42. The film forming method according to claim 27, wherein said film forming composition is a manicure composition and said material to be treated is a nail.

43. A manicuring method for nails comprising the steps of; applying the manicuring composition according to claim 12 onto a nail; and dipping said nail in water to form a solidified film in water on the nail.

44. The manicuring method according to claim 43, wherein the time for dipping the nail in water is in less than 2 minutes.

45. A manicuring method for nails comprising the steps of: applying the manicuring composition according to claim 19 onto a nail; and dipping said nail in water to form a solidified film in water on the nail.

46. The manicuring method according to claim 45, wherein the time for dipping the nail in water is in less than 2 minutes.

* * * * *